(12) United States Patent
Dean et al.

(10) Patent No.: US 7,375,212 B2
(45) Date of Patent: May 20, 2008

(54) MODULATION OF AURORA B EXPRESSION

(75) Inventors: Nicholas M. Dean, Olivenhain, CA (US); Kenneth W. Dobie, Del Mar, CA (US); Erich Koller, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 281 days.

(21) Appl. No.: 11/136,815

(22) Filed: May 24, 2005

(65) Prior Publication Data

US 2005/0267065 A1    Dec. 1, 2005

Related U.S. Application Data

(60) Provisional application No. 60/671,903, filed on Apr. 15, 2005, provisional application No. 60/574,053, filed on May 24, 2004.

(51) Int. Cl.
  *C07H 21/02* (2006.01)
  *C07H 21/04* (2006.01)
  *A61K 31/70* (2006.01)
(52) U.S. Cl. .......................... 536/24.5; 435/6; 514/44; 536/23.1; 536/24.1
(58) Field of Classification Search ............... None
  See application file for complete search history.

(56) References Cited

U.S. PATENT DOCUMENTS 5,998,148 A * 12/1999 Bennett et al. ............. 435/6
6,759,212 B1 * 7/2004 Tatsuka et al. ............. 435/69.1
2005/0107386 A1 * 5/2005 Narla et al. ................ 514/243

OTHER PUBLICATIONS

Adams, R. R. et al., "Chromosomal passengers and the (aurora) ABCs of mitosis," *Trends in Cell Biol.* (2001) 11(2):49-54.
Andrews, P. D. et al., "Aurora B Regulates MCAK at the Mitotic Centromere," *Dev. Cell.* (2004) 6:253-268.
Carmena, M. et al., "The Cellular Geography of Aurora Kinases," *Nature Rev. Mol. Cell. Biol.* (2003) 4:842-854.
Chen, J. et al., "Survivin Enhances Aurora-B Kinase Activity and Localizes Aurora-B in Human Cells," *J. Biol. Chem.* (2003) 278(1):486-490.
Giet, R. et al., "Aurora/Ip11p-related kinases, a new oncogenic family of mitotic serine-threonin kinases," *J. Cell. Sci.* (1999) 112:3591-3601.
Giet, R. et al., "*Drosophila* Aurora B Kinase is Required for Histone H3 Phosphorylation and Condensin Recruitment during Chromosome Condensation and to Organize the Central Spindle during Cytokinesis," *J. Cell. Biol.* (2001) 152(4):669-681.

Harrington, E. A. et al., "VX-680, a potent and selective small-molecule inhibitor of the Aurora kinases, suppresses tumor growth in vivo," *Nature Med.* (2004) 10(3):262-267.
Hauf, S. et al., "The small molecule Hesperadin reveals a role for Aurora B in correcting kinetochore-microtubule attachment and in maintaining the spindle assembly checkpoint," *J. Cell Biol.* (2003) 161(2):281-294.
Honda, R. et al., "Exploring the Functional Interactions between Aurora B, INCENP, and Survivin in Mitosis," *Mol. Biol. Cell* (2003) 14:3325-3341.
Lampson, M. A. et al., "Correcting improper chromosome-spindle attachments during cell division," *Nature Cell Biol.* (2004) 6(3):232-237.
Lampson, M. A. et al., "The human mitotic checkpoint protein BubR1 regulates chromosome-spindle attachments," *Nature Cell Biol.* (2005) 7(1):93-98.
Murata-Hori, M. et al., "The Kinase Activity of Aurora B is Required for Kinetochore-Microtubule Interactions during Mitosis," *Curr. Biol.* (2002) 12:894-899.
Shannon, K. B. et al., "Chromosome Dynamics: New Light on Dispatch Aurora B Kinase Function," *Curr. Biol.* (2002) 12:R458-R460.
Shindo, M. et al., "cDNA Cloning, Expression, Subcellular Localization, and Chromosomal Assignment of Mammalian Aurora Homologues, Aurora-Related Kinase (ARK) 1 and 2," *Biochem. Biophys. Res. Comm.* (1998) 244:285-292.
Tatsuka, M. et al., "Multinuclearity and Increased Ploidy Caused by Overexpression of the Aurora- and Ip11-like Midbody-associated Protein Mitotic Kinase in Human Cancer-Cells," *Cancer Res.* (1998) 58(21):4811-4816.
Terada, Y. et al., "AIM-1:a mammalian midbody-associated protein required for cytokinesis," *EMBO J.* (1998) 17(3):667-676.
Wheatley, S. P. et al., "Aurora-B Phosphorylation in Vitro Identifies a Residue of Survivin That is Essential for Its Localization and Binding to Inner Centromere Protein (INCENP) in Vivo," *J. Biol. Chem.* (2004) 279(7):5655-5660.
Zeitlin, S. G. et al., "CENP—A is phosphorylated by Aurora B kinase and plays an unexpected role in completion of cytokinesis," *J. Cell Biol.* (2001) 155(7):1147-1157.

\* cited by examiner

*Primary Examiner*—Sean McGarry
(74) *Attorney, Agent, or Firm*—Knobbe, Martens, Olson and Bear LLP

(57) ABSTRACT

Compounds, compositions and methods are provided for modulating the expression of Aurora B. The compositions comprise oligonucleotides, targeted to nucleic acid encoding Aurora B. Methods of using these compounds for modulation of Aurora B expression and for diagnosis and treatment of diseases and conditions associated with expression of Aurora B are provided. Also provided are methods of using these compounds to modulate the growth of cancer cells, including p53-deficient cancer cells.

10 Claims, No Drawings

SEQUENCE LISTING

<160> NUMBER OF SEQ ID NOS: 91

<210> SEQ ID NO 1
<211> LENGTH: 20
<212> TYPE: DNA
<213> ORGANISM: Artificial Sequence
<220> FEATURE:
<223> OTHER INFORMATION: Antisense Compound -continued

```
<400> SEQUENCE: 1
tccgtcatcg ctcctcaggg                                               20

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
gtgcgcgcga gcccgaaatc                                               20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
atgcattctg cccccaagga                                               20

<210> SEQ ID NO 4
<211> LENGTH: 1224
<212> TYPE: DNA
<213> ORGANISM: H. sapiens
<220> FEATURE:
<220> FEATURE:
<221> NAME/KEY: CDS
<222> LOCATION: (58)...(1092)

<400> SEQUENCE: 4
```

| | | | |
|---|---|---|---|
| ggccgggaga gtagcagtgc cttggacccc agctctcctc cccctttctc tctaagg | | | 57 |

| atg | gcc | cag | aag | gag | aac | tcc | tac | ccc | tgg | ccc | tac | ggc | cga | cag | acg | 105 |
|---|---|---|---|---|---|---|---|---|---|---|---|---|---|---|---|---|
| Met | Ala | Gln | Lys | Glu | Asn | Ser | Tyr | Pro | Trp | Pro | Tyr | Gly | Arg | Gln | Thr | |
| 1 | | | | 5 | | | | | 10 | | | | | 15 | | |

| gct | cca | tct | ggc | ctg | agc | acc | ctg | ccc | cag | cga | gtc | ctc | cgg | aaa | gag | 153 |
|---|---|---|---|---|---|---|---|---|---|---|---|---|---|---|---|---|
| Ala | Pro | Ser | Gly | Leu | Ser | Thr | Leu | Pro | Gln | Arg | Val | Leu | Arg | Lys | Glu | |
| | | | 20 | | | | | 25 | | | | | 30 | | | |

| cct | gtc | acc | cca | tct | gca | ctt | gtc | ctc | atg | agc | cgc | tcc | aat | gtc | cag | 201 |
|---|---|---|---|---|---|---|---|---|---|---|---|---|---|---|---|---|
| Pro | Val | Thr | Pro | Ser | Ala | Leu | Val | Leu | Met | Ser | Arg | Ser | Asn | Val | Gln | |
| | 35 | | | | | 40 | | | | | 45 | | | | | |

| ccc | aca | gct | gcc | cct | ggc | cag | aag | gtg | atg | gag | aat | agc | agt | ggg | aca | 249 |
|---|---|---|---|---|---|---|---|---|---|---|---|---|---|---|---|---|
| Pro | Thr | Ala | Ala | Pro | Gly | Gln | Lys | Val | Met | Glu | Asn | Ser | Ser | Gly | Thr | |
| 50 | | | | | 55 | | | | | 60 | | | | | | |

| ccc | gac | atc | tta | acg | cgg | cac | ttc | aca | att | gat | gac | ttt | gag | att | ggg | 297 |
|---|---|---|---|---|---|---|---|---|---|---|---|---|---|---|---|---|
| Pro | Asp | Ile | Leu | Thr | Arg | His | Phe | Thr | Ile | Asp | Asp | Phe | Glu | Ile | Gly | |
| 65 | | | | 70 | | | | | 75 | | | | | 80 | | |

| cgt | cct | ctg | ggc | aaa | ggc | aag | ttt | gga | aac | gtg | tac | ttg | gct | cgg | gag | 345 |
|---|---|---|---|---|---|---|---|---|---|---|---|---|---|---|---|---|
| Arg | Pro | Leu | Gly | Lys | Gly | Lys | Phe | Gly | Asn | Val | Tyr | Leu | Ala | Arg | Glu | |
| | | | | 85 | | | | | 90 | | | | | 95 | | |

| aag | aaa | agc | cat | ttc | atc | gtg | gcg | ctc | aag | gtc | ctc | ttc | aag | tcc | cag | 393 |
|---|---|---|---|---|---|---|---|---|---|---|---|---|---|---|---|---|
| Lys | Lys | Ser | His | Phe | Ile | Val | Ala | Leu | Lys | Val | Leu | Phe | Lys | Ser | Gln | |
| | | | 100 | | | | | 105 | | | | | 110 | | | |

| ata | gag | aag | gag | ggc | gtg | gag | cat | cag | ctg | cgc | aga | gag | atc | gaa | atc | 441 |
|---|---|---|---|---|---|---|---|---|---|---|---|---|---|---|---|---|
| Ile | Glu | Lys | Glu | Gly | Val | Glu | His | Gln | Leu | Arg | Arg | Glu | Ile | Glu | Ile | |
| | | 115 | | | | | 120 | | | | | 125 | | | | |

| cag | gcc | cac | ctg | cac | cat | ccc | aac | atc | ctg | cgt | ctc | tac | aac | tat | ttt | 489 |
|---|---|---|---|---|---|---|---|---|---|---|---|---|---|---|---|---|
| Gln | Ala | His | Leu | His | His | Pro | Asn | Ile | Leu | Arg | Leu | Tyr | Asn | Tyr | Phe | |
| 130 | | | | | 135 | | | | | 140 | | | | | | |

| tat | gac | cgg | agg | agg | atc | tac | ttg | att | cta | gag | tat | gcc | ccc | cgc | ggg | 537 |
|---|---|---|---|---|---|---|---|---|---|---|---|---|---|---|---|---|

```
Tyr Asp Arg Arg Arg Ile Tyr Leu Ile Leu Glu Tyr Ala Pro Arg Gly
145                 150                 155                 160 gag ctc tac aag gag ctg cag aag agc tgc aca ttt gac gag cag cga        585
Glu Leu Tyr Lys Glu Leu Gln Lys Ser Cys Thr Phe Asp Glu Gln Arg
                165                 170                 175 aca gcc acg atc atg gag gag ttg gca gat gct cta atg tac tgc cat        633
Thr Ala Thr Ile Met Glu Glu Leu Ala Asp Ala Leu Met Tyr Cys His
            180                 185                 190 ggg aag aag gtg att cac aga gac ata aag cca gaa aat ctg ctc tta        681
Gly Lys Lys Val Ile His Arg Asp Ile Lys Pro Glu Asn Leu Leu Leu
        195                 200                 205 ggg ctc aag gga gag ctg aag att gct gac ttc ggc tgg tct gtg cat        729
Gly Leu Lys Gly Glu Leu Lys Ile Ala Asp Phe Gly Trp Ser Val His
    210                 215                 220 gcg ccc tcc ctg agg agg aag aca atg tgt ggc acc ctg gac tac ctg        777
Ala Pro Ser Leu Arg Arg Lys Thr Met Cys Gly Thr Leu Asp Tyr Leu
225                 230                 235                 240 ccc cca gag atg att gag ggg cgc atg cac aat gag aag gtg gat ctg        825
Pro Pro Glu Met Ile Glu Gly Arg Met His Asn Glu Lys Val Asp Leu
                245                 250                 255 tgg tgc att gga gtg ctt tgc tat gag ctg ctg gtg ggg aac cca ccc        873
Trp Cys Ile Gly Val Leu Cys Tyr Glu Leu Leu Val Gly Asn Pro Pro
            260                 265                 270 ttt gag agt gca tca cac aac gag acc tat cgc cgc atc gtc aag gtg        921
Phe Glu Ser Ala Ser His Asn Glu Thr Tyr Arg Arg Ile Val Lys Val
        275                 280                 285 gac cta aag ttc ccc gct tct gtg ccc acg gga gcc cag gac ctc atc        969
Asp Leu Lys Phe Pro Ala Ser Val Pro Thr Gly Ala Gln Asp Leu Ile
    290                 295                 300 tcc aaa ctg ctc agg cat aac ccc tcg gaa cgg ctg ccc ctg gcc cag       1017
Ser Lys Leu Leu Arg His Asn Pro Ser Glu Arg Leu Pro Leu Ala Gln
305                 310                 315                 320 gtc tca gcc cac cct tgg gtc cgg gcc aac tct cgg agg gtg ctg cct       1065
Val Ser Ala His Pro Trp Val Arg Ala Asn Ser Arg Arg Val Leu Pro
                325                 330                 335 ccc tct gcc ctt caa tct gtc gcc tga tggtccctgt cattcactcg              1112
Pro Ser Ala Leu Gln Ser Val Ala
            340 ggtgcgtgtg tttgtatgtc tgtgtatgta taggggaaag aagggatccc taactgttcc     1172 cttatctgtt ttctacctcc tcctttgttt aataaaggct gaagcttttt gt             1224

<210> SEQ ID NO 5
<211> LENGTH: 18
<212> TYPE: DNA
<213> ORGANISM: Artificial Sequence
<220> FEATURE:
<223> OTHER INFORMATION: PCR Primer

<400> SEQUENCE: 5
cagcgagtcc tccggaaa                                                     18

<210> SEQ ID NO 6
<211> LENGTH: 19
<212> TYPE: DNA
<213> ORGANISM: Artificial Sequence
<220> FEATURE:
<223> OTHER INFORMATION: PCR Primer

<400> SEQUENCE: 6
acattggagc ggctcatga                                                    19
```

<210> SEQ ID NO 7
<211> LENGTH: 26
<212> TYPE: DNA
<213> ORGANISM: Artificial Sequence
<220> FEATURE:
<223> OTHER INFORMATION: PCR Probe

<400> SEQUENCE: 7
agcctgtcac cccatctgca cttgtc                                              26

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                      19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                     20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                                     20

<210> SEQ ID NO 11
<211> LENGTH: 20
<212> TYPE: DNA
<213> ORGANISM: Artificial Sequence
<220> FEATURE:
<223> OTHER INFORMATION: Antisense Compound

<400> SEQUENCE: 11
gatgtcgggt gtcccactgc                                                     20

<210> SEQ ID NO 12
<211> LENGTH: 20
<212> TYPE: DNA
<213> ORGANISM: Artificial Sequence
<220> FEATURE:
<223> OTHER INFORMATION: Antisense Compound

<400> SEQUENCE: 12
ctctctgcgc agctgatgct                                                     20

<210> SEQ ID NO 13
<211> LENGTH: 20
<212> TYPE: DNA
<213> ORGANISM: Artificial Sequence
<220> FEATURE:
<223> OTHER INFORMATION: Antisense Compound

<400> SEQUENCE: 13
cacattgtct tcctcctcag                                                      20

<210> SEQ ID NO 14
<211> LENGTH: 20
<212> TYPE: DNA
<213> ORGANISM: Artificial Sequence
<220> FEATURE:
<223> OTHER INFORMATION: Antisense Compound

<400> SEQUENCE: 14
ttcagccttt attaaacaaa                                                      20

<210> SEQ ID NO 15
<211> LENGTH: 20
<212> TYPE: DNA
<213> ORGANISM: Artificial Sequence
<220> FEATURE:
<223> OTHER INFORMATION: Antisense Compound

<400> SEQUENCE: 15
aaatgtgcag ctcttctgca                                                      20

<210> SEQ ID NO 16
<211> LENGTH: 20
<212> TYPE: DNA
<213> ORGANISM: Artificial Sequence
<220> FEATURE:
<223> OTHER INFORMATION: Antisense Compound

<400> SEQUENCE: 16
atgaaatggc ttttcttctc                                                      20

<210> SEQ ID NO 17
<211> LENGTH: 20
<212> TYPE: DNA
<213> ORGANISM: Artificial Sequence
<220> FEATURE:
<223> OTHER INFORMATION: Antisense Compound

<400> SEQUENCE: 17
aagtcatcaa ttgtgaagtg                                                      20

<210> SEQ ID NO 18
<211> LENGTH: 20
<212> TYPE: DNA
<213> ORGANISM: Artificial Sequence
<220> FEATURE:
<223> OTHER INFORMATION: Antisense Compound

<400> SEQUENCE: 18
ctctcccttg agccctaaga                                                      20

<210> SEQ ID NO 19
<211> LENGTH: 20
<212> TYPE: DNA
<213> ORGANISM: Artificial Sequence
<220> FEATURE:
<223> OTHER INFORMATION: Antisense Compound

<400> SEQUENCE: 19
gcgcatgcac agaccagccg                                                      20

<210> SEQ ID NO 20

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 20
caatctcaaa gtcatcaatt                                                     20

<210> SEQ ID NO 21
<211> LENGTH: 20
<212> TYPE: DNA
<213> ORGANISM: Artificial Sequence
<220> FEATURE:
<223> OTHER INFORMATION: Antisense Compound

<400> SEQUENCE: 21
gttgtagaga cgcaggatgt                                                     20

<210> SEQ ID NO 22
<211> LENGTH: 20
<212> TYPE: DNA
<213> ORGANISM: Artificial Sequence
<220> FEATURE:
<223> OTHER INFORMATION: Antisense Compound

<400> SEQUENCE: 22
ctcctccggt cataaaaata                                                     20

<210> SEQ ID NO 23
<211> LENGTH: 20
<212> TYPE: DNA
<213> ORGANISM: Artificial Sequence
<220> FEATURE:
<223> OTHER INFORMATION: Antisense Compound

<400> SEQUENCE: 23
gggaccatca ggcgacagat                                                     20

<210> SEQ ID NO 24
<211> LENGTH: 20
<212> TYPE: DNA
<213> ORGANISM: Artificial Sequence
<220> FEATURE:
<223> OTHER INFORMATION: Antisense Compound

<400> SEQUENCE: 24
tgttcgctgc tcgtcaaatg                                                     20

<210> SEQ ID NO 25
<211> LENGTH: 20
<212> TYPE: DNA
<213> ORGANISM: Artificial Sequence
<220> FEATURE:
<223> OTHER INFORMATION: Antisense Compound

<400> SEQUENCE: 25
tcagctctcc cttgagccct                                                     20

<210> SEQ ID NO 26
<211> LENGTH: 20
<212> TYPE: DNA
<213> ORGANISM: Artificial Sequence
<220> FEATURE:
<223> OTHER INFORMATION: Antisense Compound

<400> SEQUENCE: 26
```
ccaagtacac gtttccaaac                                              20

<210> SEQ ID NO 27
<211> LENGTH: 20
<212> TYPE: DNA
<213> ORGANISM: Artificial Sequence
<220> FEATURE:
<223> OTHER INFORMATION: Antisense Compound

<400> SEQUENCE: 27
tgagcagttt ggagatgagg                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense Compound

<400> SEQUENCE: 28
acagggacca tcaggcgaca                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29
tccttctggg ccatccttag                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense Compound

<400> SEQUENCE: 30
ggagggcgca tgcacagacc                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31
attgtgaagt gccgcgttaa                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Compound

<400> SEQUENCE: 32
aggagttctc cttctgggcc                                              20

<210> SEQ ID NO 33
<211> LENGTH: 20
<212> TYPE: DNA

```
<213> ORGANISM: Artificial Sequence
<220> FEATURE:
<223> OTHER INFORMATION: Antisense Compound

<400> SEQUENCE: 33
gcgataggtc tcgttgtgtg                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34
ttcttcccat ggcagtacat                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Compound

<400> SEQUENCE: 35
ccatccttag agagaaaggg                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Compound

<400> SEQUENCE: 36
ggagcggctc atgaggacaa                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
aacacacgca cccgagtgaa                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
tgacaggctc tttccggagg                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Compound

<400> SEQUENCE: 39
ggcactgcta ctctcccggc                                              20
```

```
<210> SEQ ID NO 40
<211> LENGTH: 20
<212> TYPE: DNA
<213> ORGANISM: Artificial Sequence
<220> FEATURE:
<223> OTHER INFORMATION: Antisense Compound

<400> SEQUENCE: 40
gttctccttc tgggccatcc                                           20

<210> SEQ ID NO 41
<211> LENGTH: 20
<212> TYPE: DNA
<213> ORGANISM: Artificial Sequence
<220> FEATURE:
<223> OTHER INFORMATION: Antisense Compound

<400> SEQUENCE: 41
cccctataca tacacagaca                                           20

<210> SEQ ID NO 42
<211> LENGTH: 20
<212> TYPE: DNA
<213> ORGANISM: Artificial Sequence
<220> FEATURE:
<223> OTHER INFORMATION: Antisense Compound

<400> SEQUENCE: 42
gctctccctt gagccctaag                                           20

<210> SEQ ID NO 43
<211> LENGTH: 20
<212> TYPE: DNA
<213> ORGANISM: Artificial Sequence
<220> FEATURE:
<223> OTHER INFORMATION: Antisense Compound

<400> SEQUENCE: 43
ctcccgtggg cacagaagcg                                           20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
catgcgcccc tcaatcatct                                           20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound

<400> SEQUENCE: 45
gtacacgttt ccaaacttgc                                           20

<210> SEQ ID NO 46
<211> LENGTH: 20
<212> TYPE: DNA
<213> ORGANISM: Artificial Sequence
<220> FEATURE:
```

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 46
tgtcttcctc ctcagggagg                                        20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
gcctggattt cgatctctct                                        20

<210> SEQ ID NO 48
<211> LENGTH: 20
<212> TYPE: DNA
<213> ORGANISM: H. sapiens
<220> FEATURE:

<400> SEQUENCE: 48
gcagtgggac acccgacatc                                        20

<210> SEQ ID NO 49
<211> LENGTH: 20
<212> TYPE: DNA
<213> ORGANISM: H. sapiens
<220> FEATURE:

<400> SEQUENCE: 49
agcatcagct gcgcagagag                                        20

<210> SEQ ID NO 50
<211> LENGTH: 20
<212> TYPE: DNA
<213> ORGANISM: H. sapiens
<220> FEATURE:

<400> SEQUENCE: 50
ctgaggagga agacaatgtg                                        20

<210> SEQ ID NO 51
<211> LENGTH: 20
<212> TYPE: DNA
<213> ORGANISM: H. sapiens
<220> FEATURE:

<400> SEQUENCE: 51
tttgtttaat aaaggctgaa                                        20

<210> SEQ ID NO 52
<211> LENGTH: 20
<212> TYPE: DNA
<213> ORGANISM: H. sapiens
<220> FEATURE:

<400> SEQUENCE: 52
tgcagaagag ctgcacattt                                        20

<210> SEQ ID NO 53
<211> LENGTH: 20
<212> TYPE: DNA
<213> ORGANISM: H. sapiens
<220> FEATURE:

```
<400> SEQUENCE: 53
cacttcacaa ttgatgactt                                           20

<210> SEQ ID NO 54
<211> LENGTH: 20
<212> TYPE: DNA
<213> ORGANISM: H. sapiens
<220> FEATURE:

<400> SEQUENCE: 54
tcttagggct caagggagag                                           20

<210> SEQ ID NO 55
<211> LENGTH: 20
<212> TYPE: DNA
<213> ORGANISM: H. sapiens
<220> FEATURE:

<400> SEQUENCE: 55
cggctggtct gtgcatgcgc                                           20

<210> SEQ ID NO 56
<211> LENGTH: 20
<212> TYPE: DNA
<213> ORGANISM: H. sapiens
<220> FEATURE:

<400> SEQUENCE: 56
acatcctgcg tctctacaac                                           20

<210> SEQ ID NO 57
<211> LENGTH: 20
<212> TYPE: DNA
<213> ORGANISM: H. sapiens
<220> FEATURE:

<400> SEQUENCE: 57
tatttttatg accggaggag                                           20

<210> SEQ ID NO 58
<211> LENGTH: 20
<212> TYPE: DNA
<213> ORGANISM: H. sapiens
<220> FEATURE:

<400> SEQUENCE: 58
atctgtcgcc tgatggtccc                                           20

<210> SEQ ID NO 59
<211> LENGTH: 20
<212> TYPE: DNA
<213> ORGANISM: H. sapiens
<220> FEATURE:

<400> SEQUENCE: 59
catttgacga gcagcgaaca                                           20

<210> SEQ ID NO 60
<211> LENGTH: 20
<212> TYPE: DNA
<213> ORGANISM: H. sapiens
<220> FEATURE:

<400> SEQUENCE: 60
```
gtttggaaac gtgtacttgg                    20

<210> SEQ ID NO 61
<211> LENGTH: 20
<212> TYPE: DNA
<213> ORGANISM: H. sapiens
<220> FEATURE:

<400> SEQUENCE: 61
cctcatctcc aaactgctca                    20

<210> SEQ ID NO 62
<211> LENGTH: 20
<212> TYPE: DNA
<213> ORGANISM: H. sapiens
<220> FEATURE:

<400> SEQUENCE: 62
tgtcgcctga tggtccctgt                    20

<210> SEQ ID NO 63
<211> LENGTH: 20
<212> TYPE: DNA
<213> ORGANISM: H. sapiens
<220> FEATURE:

<400> SEQUENCE: 63
ctaaggatgg cccagaagga                    20

<210> SEQ ID NO 64
<211> LENGTH: 20
<212> TYPE: DNA
<213> ORGANISM: H. sapiens
<220> FEATURE:

<400> SEQUENCE: 64
ggtctgtgca tgcgccctcc                    20

<210> SEQ ID NO 65
<211> LENGTH: 20
<212> TYPE: DNA
<213> ORGANISM: H. sapiens
<220> FEATURE:

<400> SEQUENCE: 65
ttaacgcggc acttcacaat                    20

<210> SEQ ID NO 66
<211> LENGTH: 20
<212> TYPE: DNA
<213> ORGANISM: H. sapiens
<220> FEATURE:

<400> SEQUENCE: 66
ggcccagaag gagaactcct                    20

<210> SEQ ID NO 67
<211> LENGTH: 20
<212> TYPE: DNA
<213> ORGANISM: H. sapiens
<220> FEATURE:

<400> SEQUENCE: 67
cacacaacga gacctatcgc                    20

<210> SEQ ID NO 68
<211> LENGTH: 20
<212> TYPE: DNA
<213> ORGANISM: H. sapiens
<220> FEATURE:

<400> SEQUENCE: 68
atgtactgcc atgggaagaa                                               20

<210> SEQ ID NO 69
<211> LENGTH: 20
<212> TYPE: DNA
<213> ORGANISM: H. sapiens
<220> FEATURE:

<400> SEQUENCE: 69
ccctttctct ctaaggatgg                                               20

<210> SEQ ID NO 70
<211> LENGTH: 20
<212> TYPE: DNA
<213> ORGANISM: H. sapiens
<220> FEATURE:

<400> SEQUENCE: 70
ttgtcctcat gagccgctcc                                               20

<210> SEQ ID NO 71
<211> LENGTH: 20
<212> TYPE: DNA
<213> ORGANISM: H. sapiens
<220> FEATURE:

<400> SEQUENCE: 71
ttcactcggg tgcgtgtgtt                                               20

<210> SEQ ID NO 72
<211> LENGTH: 20
<212> TYPE: DNA
<213> ORGANISM: H. sapiens
<220> FEATURE:

<400> SEQUENCE: 72
cctccggaaa gagcctgtca                                               20

<210> SEQ ID NO 73
<211> LENGTH: 20
<212> TYPE: DNA
<213> ORGANISM: H. sapiens
<220> FEATURE:

<400> SEQUENCE: 73
gccgggagag tagcagtgcc                                               20

<210> SEQ ID NO 74
<211> LENGTH: 20
<212> TYPE: DNA
<213> ORGANISM: H. sapiens
<220> FEATURE:

<400> SEQUENCE: 74
ggatggccca gaaggagaac                                               20

```
<210> SEQ ID NO 75
<211> LENGTH: 20
<212> TYPE: DNA
<213> ORGANISM: H. sapiens
<220> FEATURE:

<400> SEQUENCE: 75
tgtctgtgta tgtatagggg                                               20

<210> SEQ ID NO 76
<211> LENGTH: 20
<212> TYPE: DNA
<213> ORGANISM: H. sapiens
<220> FEATURE:

<400> SEQUENCE: 76
cttagggctc aagggagagc                                               20

<210> SEQ ID NO 77
<211> LENGTH: 20
<212> TYPE: DNA
<213> ORGANISM: H. sapiens
<220> FEATURE:

<400> SEQUENCE: 77
cgcttctgtg cccacgggag                                               20

<210> SEQ ID NO 78
<211> LENGTH: 20
<212> TYPE: DNA
<213> ORGANISM: H. sapiens
<220> FEATURE:

<400> SEQUENCE: 78
agatgattga ggggcgcatg                                               20

<210> SEQ ID NO 79
<211> LENGTH: 20
<212> TYPE: DNA
<213> ORGANISM: H. sapiens
<220> FEATURE:

<400> SEQUENCE: 79
gcaagtttgg aaacgtgtac                                               20

<210> SEQ ID NO 80
<211> LENGTH: 20
<212> TYPE: DNA
<213> ORGANISM: H. sapiens
<220> FEATURE:

<400> SEQUENCE: 80
cctccctgag gaggaagaca                                               20

<210> SEQ ID NO 81
<211> LENGTH: 20
<212> TYPE: DNA
<213> ORGANISM: H. sapiens
<220> FEATURE:

<400> SEQUENCE: 81
agagagatcg aaatccaggc                                               20

<210> SEQ ID NO 82
<211> LENGTH: 20
```

```
<212> TYPE: DNA
<213> ORGANISM: Artificial Sequence
<220> FEATURE:
<223> OTHER INFORMATION: Antisense Compound
<220> FEATURE:
<221> NAME/KEY: misc_feature
<222> LOCATION: 1-20
<223> OTHER INFORMATION: n = A,T,C or G

<400> SEQUENCE: 82
nnnnnnnnnn nnnnnnnnnn                                                      20

<210> SEQ ID NO 83
<211> LENGTH: 20
<212> TYPE: DNA
<213> ORGANISM: Artificial Sequence
<220> FEATURE:
<223> OTHER INFORMATION: Antisense Compound

<400> SEQUENCE: 83
atccaagtgc tactgtagta                                                      20

<210> SEQ ID NO 84
<211> LENGTH: 20
<212> TYPE: DNA
<213> ORGANISM: Artificial Sequence
<220> FEATURE:
<223> OTHER INFORMATION: Antisense Compound

<400> SEQUENCE: 84
ttgtcccagt cccaggcctc                                                      20

<210> SEQ ID NO 85
<211> LENGTH: 20
<212> TYPE: DNA
<213> ORGANISM: Artificial Sequence
<220> FEATURE:
<223> OTHER INFORMATION: Antisense Compound

<400> SEQUENCE: 85
gccctccatg ctggcacagg                                                      20

<210> SEQ ID NO 86
<211> LENGTH: 20
<212> TYPE: DNA
<213> ORGANISM: Artificial Sequence
<220> FEATURE:
<223> OTHER INFORMATION: Antisense Compound

<400> SEQUENCE: 86
agcaaaagat caatccgtta                                                      20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
cgtgtgtctg tgctagtccc                                                      20
```

```
<210> SEQ ID NO 88
<211> LENGTH: 19
<212> TYPE: DNA
<213> ORGANISM: Artificial Sequence
<220> FEATURE:
<223> OTHER INFORMATION: Oligomeric Compound

<400> SEQUENCE: 88
cgagaggcgg acgggaccg                                               19

<210> SEQ ID NO 89
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 89
cgagaggcgg acgggaccgt t                                            21

<210> SEQ ID NO 90
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 90
ttgctctccg cctgccctgg c                                            21

<210> SEQ ID NO 91
<211> LENGTH: 19
<212> TYPE: DNA
<213> ORGANISM: Artificial Sequence
<220> FEATURE:
<223> OTHER INFORMATION: Oligomeric Compound

<400> SEQUENCE: 91
gctctccgcc tgccctggc                                               19
```

MODULATION OF AURORA B EXPRESSION

CROSS REFERENCE TO RELATED APPLICATIONS

This application claims the benefit of priority of U.S. Provisional Application Ser. No. 60/574,053, filed May 24, 2004, and U.S. Provisional Application Ser. No. 60/671,903, filed Apr. 15, 2005, each of which is herein incorporated by reference in its entirety.

SEQUENCE LISTING

A paper copy of the sequence listing and a computer-readable form of the sequence listing, on diskette, containing the file named HTS0034USSEQ.txt, which was created on May 24, 2005, are herein incorporated by reference.

FIELD OF THE INVENTION

The present invention provides compositions and methods for modulating the expression of Aurora B. In particular, this invention relates to antisense compounds, particularly oligonucleotide compounds, which, in preferred embodiments, hybridize with nucleic acid molecules encoding Aurora B. Such compounds are shown herein to modulate the expression of Aurora B. Such compounds further modulate the growth of cancer cells, including p53-deficient cancer cells.

BACKGROUND OF THE INVENTION

Cell division, which includes the process of nuclear division (mitosis) and the process of cytoplasmic division (cytokinesis), is initiated at the molecular level by a cascade of protein phosphorylations. The kinases catalyzing the phosphorylation events therefore mediate the many morphological changes that accompany mitosis. During cell division, the chromosomes condense, the nuclear envelope dissolves, the cell detaches from neighboring cells and the extracellular matrix, and the cytoskeleton rearranges to organize the movements necessary to segregate the chromosomes and ultimately divide the cell into two. Because faithful replication and division of the genetic material is crucial to propagation of physiologically functional cells, considerable attention has been devoted to the characterization of proteins exhibiting kinase enzymatic activity during mitosis. A number of disease states and/or disorders may result from cell division errors arising from either aberrant activation or functional mutations in the molecular components of the kinase cascades. For example, cell division errors result in hyperproliferative disorders, such as cancer.

A mutation in a *Drosophila* serine/threonine kinase, designated aurora, was found to be responsible for a chromosomal segregation error arising from defective spindle-pole behavior. Several Aurora-like kinases have since been identified in a number of organisms. A single Aurora named Ipl1 (Increase-in-ploidy 1) was identified in *Saccharomyces cerevisiae* in a genetic screen for mutants that were defective in chromosome segregation. *Schizosaccharomyces pombe* also has a single Aurora called Aurora-related kinase (Ark1). Aurora is thus the name given to a family of serine-threonine protein kinases that regulate many processes during cell division. In general, aurora kinases are involved in the control of the centrosome and nuclear cycles, and appear to function in mitotic processes including chromosome condensation, spindle dynamics, kinetochore-microtubule interactions, chromosome orientation, and establishment of the metaphase plate. They are also involved in cytokinesis. Three family members (Aurora A, B, and C) have been identified independently, and the nomenclature designates the original *Drosophila* Aurora kinase as Aurora A (Carmena and Earnshaw, *Nat. Rev. Mol. Cell. Biol.*, 2003, 4, 842-854).

Using a PCR-based method to screen for novel serine/threonine kinases, the cDNAs encoding mouse and human Aurora B (also known as serine/threonine kinase 12 AIK2; AIM-1; AIM1; AIRK-2; ARK2; Aurora/IPL1-like kinase 2; HsAurora-1; STK12) were isolated. The Aurora B protein contains a kinase domain with high homology to the catalytic domain of other serine/threonine kinases (Shindo et al., *Biochem. Biophys. Res. Commun.*, 1998, 244, 285-292). A kinase-negative mutant was shown to induce a failure in cytokinesis during mitosis, indicting mammalian Aurora B in mitotic processes (Terada et al., *EMBO J.*, 1998, 17, 667-676). The Aurora B gene maps to chromosome 17p13, a region that is deleted in various cancers (Giet and Prigent, *J. Cell Sci.*, 1999, 112 (Pt 21), 3591-3601), however high levels of expression are found in cell lines from colorectal tumors (Tatsuka et al., *Cancer Res.*, 1998, 58, 4811-4816), making Aurora B an attractive target for anti-cancer therapies.

Subsequent studies have shown that aurora B kinases form a complex with at least two other proteins, the inner centromere protein (INCENP) and survivin. These proteins behave as "chromosomal passenger" proteins, first localizing along the chromosomes during prophase before concentrating at the centromere during prometaphase. During anaphase, the complex relocates to the central spindle. It is thought that the active component in the passenger complex is the Aurora B kinase, and indeed, Aurora B can phosphorylate survivin in vitro at a site important for the in vivo localization of survivin in human cells (Wheatley et al., *J. Biol. Chem.*, 2004, 279, 5655-5660). However, survivin has been shown to enhance Aurora B kinase activity and to localize Aurora B to its substrates during the cell cycle (Chen et al., *J. Biol. Chem.*, 2003, 278, 486-490). Likewise, INCEP is both a substrate and an enhancer of the kinase (Carmena and Earnshaw, *Nat. Rev. Mol. Cell. Biol.*, 2003, 4, 842-854; Honda et al., *Mol. Biol. Cell*, 2003, 14, 3325-3341). The phase-dependent localization of the complex coupled with Aurora B functional studies suggest that the protein is involved in chromosome structure and alignment as well as in coordinating anaphase and cytokinesis (Adams et al., *Trends Cell Biol.*, 2001, 11, 49-54; Shannon and Salmon, *Curr. Biol.*, 2002, 12, R458-460).

Several studies have further confirmed the importance of mammalian Aurora B in several different stages of cell division. Expression of a dominant negative mutant of Aurora B lacking kinase activity in mammalian NRK tissue cells caused multiple defects in the mitotic machinery. Notably, centromere movement was altered, and kinetochores became separated from spindle microtubles. Levels of the motor proteins dynein and CENP-E were diminished at prometaphase kinetochores, suggesting that Aurora B kinase activity plays a major role in the kinetochore assembly pathway (Murata-Hori and Wang, *Curr. Biol.*, 2002, 12, 894-899). Antisense DNA depletion of mitotic centromere-associated kinesin (MCAK), another Aurora B substrate, in mammalian cells has been shown to inhibit anaphase A. Disruption of Aurora B kinase function by expression of a kinase-dead mutant or RNAi prevented centromeric targeting of MCAK, while Aurora B phosphorylation of MCAK actually inhibits its microtubule depolymerizing activity in vitro, an action which may prevent reversal of the initial microtubule-kinetochore attachments (Andrews et al., *Dev. Cell*, 2004, 6, 253-268). CENP-A, a histone H3 variant and kinetochore protein, is a known target of Aurora B. However, mutations affecting the phosphorylation of this protein do not disrupt mitosis, but do prevent completion of cytokinesis (Zeitlin et al., *J. Cell. Biol.*, 2001, 155, 1147-1157).

The two sister kinetochores on each chromosome must become attached to opposing spindle poles for proper segregation of replicated chromatids. If a kinetochore is unattached under normal conditions, anaphase is suppressed by the spindle assembly checkpoint. If both sister kinetochores become attached to the same pole, the monoorientation would result in improper segregation. Studies with hesperadin, a small molecule inhibitor of Aurora B, suggest that the kinase is required to generate unattached kinetochores on monooriented chromosomes, thus promoting bipolar attachment and maintaining checkpoint signalling (Hauf et al., *J. Cell Biol.*, 2003, 161, 281-294). Exploiting the reversibility of small-molecule inhibitors of Aurora kinase activity, hesperadin and Aurora kinase inhibitor-1, it was demonstrated that controlled activation of Aurora kinases resulted in correction of chromosome attachment errors by selective disassembly of kinetochore-microtubule fibers (Lampson et al., *Nat. Cell Biol.*, 2004, 6, 232-237). Thus Aurora B functions to maintain genome integrity during cell division not only by coordinating kinetochore assembly, but also by correcting attachment errors thus enabling the spindle assembly checkpoint (Hauf et al., *J. Cell Biol.*, 2003, 161, 281-294; Lampson et al., *Nat. Cell Biol.*, 2004, 6, 232-237).

The myriad roles of Aurora B in cell division make it an attractive target for therapeutic and investigative strategies aimed at disorders of cell proliferation, including hyperproliferative disorders. Consequently, there remains a need for agents capable of effectively modulating Aurora B function.

Antisense technology is an effective means for reducing the expression of specific gene products and is therefore uniquely useful in a number of therapeutic, diagnostic, and research applications for the modulation of Aurora B expression.

The present invention provides compositions and methods for modulating Aurora B expression.

SUMMARY OF THE INVENTION

The present invention is directed to antisense compounds, especially nucleic acid and nucleic acid-like oligomers, which are targeted to a nucleic acid encoding Aurora B, and which modulate the expression of Aurora B. Pharmaceutical and other compositions comprising the compounds of the invention are also provided. Further provided are methods of screening for modulators of Aurora B and methods of modulating the expression of Aurora B in cells, tissues or animals comprising contacting said cells, tissues or animals with one or more of the compounds or compositions of the invention. Also provide are methods for modulating the growth of cancer cells, including p53-deficient cancer cells, comprising contacting the cells with an antisense compound targeted to a nucleic acid molecule encoding Aurora B. Such modulation of cell growth is useful for inhibiting cancer cell growth, as well as for sensitizing cancer cells to a chemotherapeutic agent. Methods of treating an animal, particularly a human, suspected of having or being prone to a disease or condition associated with expression of Aurora B are also set forth herein. Such methods comprise administering a therapeutically or prophylactically effective amount of one or more of the compounds or compositions of the invention to the person in need of treatment.

In one embodiment, oligomeric compounds targeting Aurora B are useful for the treatment of hyperproliferative disorders, including, but not limited to, breast cancer, pancreatic cancer, colon cancer, ovarian cancer, thyroid cancer, cervical cancer, prostate cancer, head and neck cancer, lung cancer, myelomas, hepatocellular carcinoma, lymphomas and leukemias.

In one aspect, the invention provides an antisense compound that is specifically hybridizable with a 5'-untranslated region (5'UTR) of a nucleic acid molecule encoding Aurora B. In another aspect, the invention provides an antisense compound comprises an antisense nucleic acid molecule that is specifically hybridizable with a start region of a nucleic acid molecule encoding Aurora B. In a further aspect, the invention provides an antisense compound comprises an antisense nucleic acid molecule that is specifically hybridizable with a coding region of a nucleic acid molecule encoding Aurora B. In another aspect, the invention provides an antisense compound comprises an antisense nucleic acid molecule that is specifically hybridizable With a stop region of a nucleic acid molecule encoding Aurora B. In an additional aspect, the invention provides an antisense compound comprises an antisense nucleic acid molecule that is specifically hybridizable with a 3'-untranslated region of a nucleic acid molecule encoding Aurora B.

The invention contemplates a diagnostic method for identifying a disease state comprising identifying the presence of Aurora B in a sample using at least one of the primers comprising SEQ ID NOs 5 or 6, or the probe comprising SEQ ID NO: 7. The invention further embodies a kit or assay device comprising the antisense compound that is specifically hybridizable with a nucleic acid molecule encoding aurora B.

DETAILED DESCRIPTION OF THE INVENTION

A. Overview of the Invention

The present invention employs antisense compounds, preferably oligonucleotides and similar species for use in modulating the function or effect of nucleic acid molecules encoding Aurora B. This is accomplished by providing oligonucleotides which specifically hybridize with one or more nucleic acid molecules encoding Aurora B. As used herein, the terms "target nucleic acid" and "nucleic acid molecule encoding Aurora B" have been used for convenience to encompass DNA encoding Aurora B, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of Aurora B. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, homology, sequence identity or complementarity, between the oligomeric and target is between about 50% to about 60%. In some embodiments, homology, sequence identity or complementarity, is between about 60% to about 70%. In further embodiments, homology, sequence identity or complementarity, is between about 70% and about 80%. In further embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%.

B. Compounds of the Invention

According to the present invention, antisense compounds include antisense oligomeric compounds, antisense oligonucleotides, siRNAs, external guide sequence (EGS) oligonucleotides, alternate splicers, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the one form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697).

The antisense compounds of the present invention also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound. These compounds are then tested using the methods described herein to determine their ability to inhibit expression of Aurora B mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the antisense compounds of this invention, the present invention comprehends other families of antisense compounds as well, including but not limited to oligonucleotide analogs and mimetics such as those described herein.

The antisense compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one embodiment, the antisense compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30; 31, 32, 33; 34, 35, 36, 37, 38, 39, 40, 41, 42, 43, 44, 45, 46, 47, 48, 49, or 50 nucleobases in length:

In one embodiment, the antisense compounds of the invention have antisense portions of 13 to 40 nucleobases. One having ordinary skill in the art will appreciate that this embodies antisense compounds having antisense portions of 13, 14, 15, 16, 17, 18, 19, 20, 21, 22, 23, 24, 25, 26, 27, 28, 29 30, 31, 32, 33, 34, 35, 36, 37, 38, 39, or 40 nucleobases.

In another embodiment, the antisense compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particular compounds are oligonucleotides from about 12 to about 50 nucleobases, from about 13 to 40 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). It is also understood that preferred antisense compounds may be represented by oligonucleotide sequences that comprise at least 8 consecutive nucleobases from an internal portion of the sequence of an illustrative preferred antisense compound, and may extend in either or both directions until the oligonucleotide contains about 8 to about 80 nucleobases.

One having skill in the art armed with the preferred antisense compounds illustrated herein will be able, without undue experimentation, to identify further preferred antiserise compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes Aurora B.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Aurora B, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the sites where exons are joined. Targeting exon-exon junctions can be useful in situations where the overproduction of a normal splice product is implicated in disease, or where the overproduction of an aberrant splice product is implicated in disease. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources known as "fusion transcripts" are also suitable target sites. It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). It is also understood that preferred antisense target segments may be represented by DNA or RNA sequences that comprise at least 8 consecutive nucleobases from an internal portion of the sequence of an illustrative preferred target segment, and may extend in either or both directions until the oligonucleotide contains about 8 to about 80 nucleobases. One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric antisense compounds can also be targeted to regions of a target nucleobase sequence, such as those disclosed herein (e.g. in Example 13). All regions of a nucleobase sequence to which an oligomeric antisense compound can be targeted, wherein the regions are greater than or equal to 8 and less than or equal to 80 nucleobases, are described as follows:

Let R(n, n+m−1) be a region from a target nucleobase sequence, where "n" is the 5'-most nucleobase position of the region, where "n+m−1" is the 3'-most nucleobase position of the region and where "m" is the length of the region. A set "S(m)", of regions of length "m" is defined as the regions where n ranges from 1 to L−m+1, where L is the length of the target nucleobase sequence and L>m. A set, "A", of all regions can be constructed as a union of the sets of regions for each length from where m is greater than or equal to 8 and is less than or equal to 80.

This set of regions can be represented using the following mathematical notation:

$$A = \bigcup_m S(m) \text{ where } m \in N \mid 8 \leq m \leq 80$$

and $$S(m) = \{R_{n,n+m-1} \mid n \in \{1,2,3,\ldots,L-m+1\}\}$$

where the mathematical operator | indicates "such that", where the mathematical operator ∈ indicates "a member of a set" (e.g. y ∈ Z indicates that element y is a member of set Z), where x is a variable, where N indicates all natural numbers, defined as positive integers, and where the mathematical operator ∪ indicates "the union of sets".

For example, the set of regions for m equal to 8, 20 and 80 can be constructed in the following manner. The set of regions, each 8 nucleobases in length, S(m=8), in a target nucleobase sequence 100 nucleobases in length (L=100), beginning at position 1 (n=1) of the target nucleobase sequence, can be created using the following expression:

$$S(8) = \{R_{1,8} \mid n \in \{1,2,3,\ldots,93\}\}$$

and describes the set of regions comprising nucleobases 1-8, 2-9, 3-10, 4-11, 5-12, 6-13, 7-14, 8-15, 9-16, 10-17, 11-18, 12-19, 13-20, 14-21, 15-22, 16-23, 17-24, 18-25, 19-26, 20-27, 21-28, 22-29, 23-30, 24-31, 25-32, 26-33, 27-34, 28-35, 29-36, 30-37, 31-38, 32-39, 33-40, 34-41, 35-42, 36-43, 37-44, 38-45, 39-46, 40-47, 41-48, 42-49, 43-50, 44-51, 45-52, 46-53, 47-54, 48-55, 49-56, 50-57, 51-58, 52-59, 53-60, 54-61, 55-62, 56-63, 57-64, 58-65, 59-66, 60-67, 61-68, 62-69, 63-70, 64-71, 65-72, 66-73, 67-74, 68-75, 69-76, 70-77, 71-78, 72-79, 73-80, 74-81, 75-82, 76-83, 77-84, 78-85, 79-86, 80-87, 81-88, 82-89, 83-90, 84-91, 85-92, 86-93, 87-94, 88-95, 89-96, 90-97, 91-98, 92-99, 93-100.

An additional set for regions 20 nucleobases in length, in a target sequence 100 nucleobases in length, beginning at position 1 of the target nucleobase sequence, can be described using the following expression:

$$S(20) = \{R_{1,20} \mid n \in \{1,2,3,\ldots,81\}\}$$

and describes the set of regions comprising nucleobases 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100.

An additional set for regions 80 nucleobases in length, in a target sequence 100 nucleobases in length, beginning at position 1 of the target nucleobase sequence, can be described using the following expression:

$$S(80) = \{R_{1,80} | n \in \{1,2,3,\ldots,21\}\}$$

and describes the set of regions comprising nucleobases 1-80, 2-81, 3-82, 4-83, 5-84, 6-85, 7-86, 8-87, 9-88, 10-89, 11-90, 12-91, 13-92, 14-93, 15-94, 16-95, 17-96, 18-97, 19-98, 20-99, 21-100.

Thus, in this example, A would include regions 1-8,2-9, 3-10.93-100, 1-20, 2-21, 3-22 . . . 81-100, 1-80, 2-81, 3-82 . . . 21-100.

The union of these aforementioned example sets and other sets for lengths from 10 to 19 and 21 to 79 can be described using the mathematical expression $$A = \bigcup_m S(m)$$

where $\bigcup$ represents the union of the sets obtained by combining all members of all sets.

The mathematical expressions described herein defines all possible target regions in a target nucleobase sequence of any length L, where the region is of length m, and where m is greater than or equal to 8 and less than or equal to 80 nucleobases and, and where m is less than L, and where n is less than L−m+1.

D. Screening and Target Validation

In a further embodiment, the "preferred target segments" identified herein may be employed in a screen for additional compounds that modulate the expression of Aurora B. "Modulators" are those compounds that decrease or increase the expression of a nucleic acid molecule encoding Aurora B and which comprise at least an 8-nucleobase portion which is complementary to a preferred target segment. The screening method comprises the steps of contacting a preferred target segment of a nucleic acid molecule encoding Aurora B with one or more candidate modulators, and selecting for one or more candidate modulators which decrease or increase the expression of a nucleic acid molecule encoding Aurora B. Once it is shown that the candidate modulator or modulators are capable of modulating (e.g. either decreasing or increasing) the expression of a nucleic acid molecule encoding Aurora B, the modulator may then be employed in further investigative studies of the function of Aurora B, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processsing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The antisense compounds of the present invention can also be applied in the areas of drug discovery and target validation. The present invention comprehends the use of the compounds and preferred target segments identified herein in drug discovery efforts to elucidate relationships that exist between Aurora B and a disease state, phenotype, or condition. These methods include detecting or modulating Aurora B comprising contacting a sample, tissue, cell, or organism with the compounds of the present invention, measuring the nucleic acid or protein level of Aurora B and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The antisense compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98;

Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The antisense compounds of the invention are useful for research and diagnostics, because these compounds hybridize to nucleic acids encoding Aurora B. The primers and probes disclosed herein are useful in methods requiring the specific detection of nucleic acid molecules encoding Aurora B and in the amplification of said nucleic acid molecules for detection or for use in further studies of Aurora B. Hybridization of the primers and probes with a nucleic acid encoding Aurora B can be detected by means known in the art. Such means may include conjugation of an enzyme to the primer or probe, radiolabelling of the primer or probe or any other suitable detection means. Kits using such detection means for detecting the level of Aurora B in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of Aurora B is treated by administering antisense compounds in accordance with this invention. For example, in one non-limiting embodiment, the methods comprise the step of administering to the animal in need of treatment, a therapeutically effective amount of a Aurora B inhibitor. The Aurora B inhibitors of the present invention effectively inhibit the activity of the Aurora B protein or inhibit the expression of the Aurora B protein. In one embodiment, the activity or expression of Aurora B in an animal is inhibited by about 10%. Preferably, the activity or expression of Aurora B in an animal is inhibited by about 30%. More preferably, the activity or expression of Aurora B in an animal is inhibited by 50% or more. Thus, the oligomeric antisense compounds modulate expression of Aurora B mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of Aurora B may be measured in serum, adipose tissue, liver or any other body fluid, tissue or organ of the animal. Preferably, the cells contained within said fluids, tissues or organs being analyzed contain a nucleic acid molecule encoding Aurora B protein and/or the Aurora B protein itself.

The antisense compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriaminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-mimetics

In other preferred antisense compounds, e.g., oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500.

Further embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified antisense compounds may also contain one or more substituted sugar moieties. Preferred are antisense compounds, preferably antisense oligonucleotides, comprising one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$ $CH_3$, O($CH_2$)$_n$O$CH_3$, O($CH_2$)$_n$N$H_2$, O($CH_2$)$_n$$CH_3$, O($CH_2$)$_n$ON$H_2$, and O($CH_2$)$_n$ON[($CH_2$)$_n$$CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-O-methoxyethyl (2'-O—$CH_2CH_2OCH_3$, also known as 2'-O-(2-methoxyethyl) or 2'-methoxyethoxy or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other modifications include 2'-methoxy (2'-O—$CH_3$), 2'-aminopropoxy (2'-O$CH_2CH_2CH_2NH_2$), 2'-allyl (2'-$CH_2$—CH═$CH_2$), 2'-O-allyl (2'-O—$CH_2$—CH═$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Antisense compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2 (3H)-one), phenothiazine cytidine (1H-pyrimido[5,4-b][1,4]benzothiazin-2 (3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodo-benzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl. phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. Chimeric anti sense oligonucleotides are thus a form of anti sense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Chimeric antisense compounds can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers". Such compounds have also been referred to in the art as hybrids. In a gapmer that is 20 nucleotides in length, a gap or wing can be 1, 2, 3, 4, 5, 6, 7, 8, 9, 10, 11, 12, 13, 14, 15, 16, 17 or 18 nucleotides in length. In one embodiment, a 20-nucleotide gapmer is comprised of a gap 8 nucleotides in length, flanked on both the 5' and 3' sides by wings 6 nucleotides in length. In another embodiment, a 20-nucleotide gapmer is comprised of a gap 10 nucleotides in length, flanked on both the 5' and 3' sides by wings 5 nucleotides in length. In another embodiment, a 20-nucleotide gapmer is comprised of a gap 12 nucleotides in length flanked on both the 5' and 3' sides by wings 4 nucleotides in length. In a further embodiment, a 20-nucleotide gapmer is comprised of a gap 14 nucleotides in length flanked on both the 5' and 3' sides by wings 3 nucleotides in length. In another embodiment, a 20-nucleotide gapmer is comprised of a gap 16 nucleotides in length flanked on both the 5' and 3' sides by wings 2 nucleotides in length. In a further embodiment, a 20-nucleotide gapmer is comprised of a gap 18 nucleotides in length flanked on both the 5' and 3' ends by wings 1 nucleotide in length. Alternatively, the wings are of different lengths, for example, a 20-nucleotide gapmer may be comprised of a gap 10 nucleotides in length, flanked by a 6-nucleotide wing on one side (5' or 3') and a 4-nucleotide wing on the other side (5' or 3').

In a hemimer, an "open end" chimeric antisense compound, 20 nucleotides in length, a gap segment, located at either the 5' or 3' terminus of the oligomeric compound, can be 1, 2, 3, 4, 5, 6, 7, 8, 9, 10, 11, 12, 13, 14, 15, 16, 17, 18 or 19 nucleotides in length. For example, a 20-nucleotide hemimer can have a gap segment of 10 nucleotides at the 5' end and a second segment of 10 nucleotides at the 3' end. Alternatively, a 20-nucleotide hemimer can have a gap segment of 10 nucleotides at the 3' end and a second segment of 10 nucleotides at the 5' end.

Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The oligomeric compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including but not limited to ophthalmic and to mucous membranes including vaginal and rectal delivery), pulmonary, e.g., by inhalation or insufflation of powders or aerosols, including by nebulizer (intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Sites of administration are known to those skilled in the art. Oligonucleotides with at least one 2'-O-methoxyethyl modification are believed to be useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Formulations for topical administration include those in which the oligomeric compounds of the invention are in admixture with a topical delivery agent such as lipids, liposomes, fatty acids, fatty acid esters, steroids, chelating agents and surfactants.

For topical or other administration, oligomeric compounds of the invention may be encapsulated within liposomes or may form complexes thereto, such as to cationic liposomes. Alternatively, oligonucleotides may be complexed to lipids, in particular to cationic lipids. Fatty acids and esters, pharmaceutically acceptable salts thereof, and their uses are further described in U.S. Pat. No. 6,287,860. Topical formulations are described in detail in U.S. patent application Ser. No. 09/315,298 filed on May 20, 1999.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

The pharmaceutical formulations and compositions of the present invention may also include surfactants. The use of surfactants in drug products, formulations and in emulsions is well known in the art. Surfactants and their uses are further described in U.S. Pat. No. 6,287,860.

In one embodiment, the present invention employs various penetration enhancers to affect the efficient delivery of oligomeric compounds, particularly oligonucleotides. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property.

Oral compositions for administration of non-parenteral oligomeric compounds can be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. Such oral oligomeric compound compositions can be referred to as "mucosal penetration enhancers."

Oligomeric compounds, such as oligonucleotides, may be delivered orally, in granular form including sprayed dried particles, or complexed to form micro or nanoparticles. Oligonucleotide complexing agents and their uses are further described in U.S. Pat. No. 6,287,860. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002.

In one embodiment, oral oligomeric compound compositions comprise at least one member of the group consisting of surfactants, fatty acids, bile salts, chelating agents, and non-chelating surfactants. Further embodiments comprise oral oligomeric compound comprising at least one fatty acid, e.g. capric or lauric acid, or combinations or salts thereof. One combination is the sodium salt of lauric acid, capric acid and UDCA.

In one embodiment, oligomeric compound compositions for oral delivery comprise at least two discrete phases, which phases may comprise particles, capsules, gel-capsules, microspheres, etc. Each phase may contain one or more oligomeric compounds, penetration enhancers, surfactants, bioadhesives, effervescent agents, or other adjuvant, excipient or diluent A "pharmaceutical carrier" or "excipient" can be a pharmaceutically acceptable solvent, suspending agent or any other pharmacologically inert vehicle for delivering one or more nucleic acids to an animal and are known in the art.

The excipient may be liquid or solid and is selected, with the planned manner of administration in mind, so as to provide for the desired bulk, consistency, etc., when combined with a nucleic acid and the other components of a given pharmaceutical composition.

Oral oligomeric compositions may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers.

One of skill in the art will recognize that formulations are routinely designed according to their intended use, i.e. route of administration.

Compositions of the invention can contain two or more oligomeric compounds. In another related embodiment, compositions of the present invention can contain one or more antisense compounds, particularly oligonucleotides, targeted to a first nucleic acid and one or more additional antisense compounds targeted to a second nucleic acid target. Alternatively, compositions of the present invention can contain two or more antisense compounds targeted to different regions of the same nucleic acid target. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, from 0.1 μg to 10 g per kg of body weight, from 1.0 μg to 1 g per kg of body weight, from 10.0 μg to 100 mg per kg of body weight, from 100 μg to 10 mg per kg of body weight, or from 1 mg to 5 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

The effects of treatments with therapeutic compositions can be assessed following collection of tissues or fluids from a patient or subject receiving said treatments. It is known in the art that a biopsy sample can be procured from certain tissues without resulting in detrimental effects to a patient or subject. In certain embodiments, a tissue and its constituent cells comprise, but are not limited to, blood (e.g., hematopoietic cells, such as human hematopoietic progenitor cells, human hematopoietic stem cells, $CD34^+$ cells $CD4^+$ cells), lymphocytes and other blood lineage cells, bone marrow, breast, cervix, colon, esophagus, lymph node, muscle, peripheral blood, oral mucosa and skin. In other embodiments, a fluid and its constituent cells comprise, but are not limited to, blood, urine, semen, synovial fluid, lymphatic fluid and cerebro-spinal fluid. Tissues or fluids procured from patients can be evaluated for expression levels of the target mRNA or protein. Additionally, the mRNA or protein expression levels of other genes known or suspected to be associated with the specific disease state, condition or phenotype can be assessed. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the disease or condition in the aforementioned tissues and fluids, collected from a patient or subject receiving treatment, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N-4-benzoyl-5-methylcytidine penultimate intermediate for 5-methyl dC amidite, [5'-O-(4,4'-Dimethoxytriphenylmethyl)-2'-deoxy-N-4-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-

Dimethoxytrityl-2'-O-(2-methoxyethyl)-5-methylcytidine intermediate, 5'-O-dimethoxytrityl-2'-O-(2-methoxyethyl)-N-4-benzoyl-5-methyl-cytidine penultimate intermediate, [5'-O-(4,4'-Dimethoxytriphenylmethyl)-2'-O-(2-methoxyethyl)-N$^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-0-(2-methoxyethyl)-N$^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-N$^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O$_2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Patent, 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleo-sides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand,.* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Compounds

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl)Phosphodiester] Chimeric Oligonucleotides

[2'-O-(2-methoxyethyl)phosphodiester]-[2'-deoxy phosphorothioate]-[2'-O-(methoxyethyl)phosphodiester] chimeric oligonucleotides are prepared as per the above procedure for the 2'-O-methyl chimeric oligonucleotide with the substitution of 2'-O-(methoxyethyl)amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting Aurora B

In accordance with the present invention, a series of nucleic acid duplexes comprising the antisense compounds of the present invention and their complements can be designed to target Aurora B. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. The antisense and sense strands of the duplex comprise from about 17 to 25 nucleotides, or from about 19 to 23 nucleotides. Alternatively, the antisense and sense strands comprise 20, 21 or 22 nucleotides.

For example, a duplex comprising an antisense strand having the sequence CGAGAGGCGGACGGGACCG (SEQ ID NO: 88) and having a two-nucleobase overhang of deoxythymidine(dT) would have the following structure:

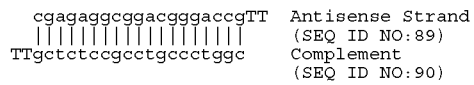
```
cgagaggcggacgggaccgTT   Antisense Strand
|||||||||||||||||||||   (SEQ ID NO:89)
TTgctctccgcctgccctggc   Complement
                        (SEQ ID NO:90)
```

Overhangs can range from 2 to 6 nucleobases and these nucleobases may or may not be complementary to the target nucleic acid. In another embodiment, the duplexes may have an overhang on only one terminus.

In another embodiment, a duplex comprising an antisense strand having the same sequence CGAGAGGCGGACGGGACCG may be prepared with blunt ends (no single stranded overhang) as shown:

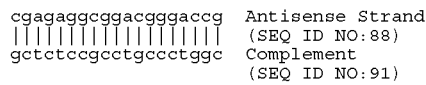
```
cgagaggcggacgggaccg    Antisense Strand
|||||||||||||||||||    (SEQ ID NO:88)
gctctccgcctgccctggc    Complement
                       (SEQ ID NO:91)
```

The RNA duplex can be unimolecular or bimolecular; i.e, the two strands can be part of a single molecule or may be separate molecules.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate Aurora B expression.

When cells reached 80% confluency, they are treated with duplexed antisense compounds of the invention. For cells grown in 96-well plates, wells are washed once with 200 μL OPTI-MEM® 1 reduced-serum medium (Invitrogen Life Technologies, Carlsbad, Calif.) and then treated with 130 μL of OPTI-MEM® 1 containing 12 μg/mL LIPOFECTIN® (Invitrogen Life Technologies, Carlsbad, Calif.) and the desired duplex antisense compound at a final concentration of 200 nM. After 5 hours of treatment, the medium is replaced with fresh medium. Cells are harvested approximately 16 hours after treatment, at which time RNA is isolated and target reduction measured by real-time PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the—16 amu product (+/−32 +/−48). For some studies oligonucleotides were purified by HPLC, as described by Chiang et al., J. Biol. Chem. 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (BECKMAN P/ACE® MDQ) or, for individually prepared samples, on a commercial CE apparatus (e.g., BECKMAN P/ACE® 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or quantitative real-time PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media supplemented with 10% fetal bovine serum, 100 units per mL penicillin, and 100 micrograms per mL streptomycin (media and supplements from Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 5500 cells/well for use in RT-PCR analysis.

A549 Cells:

The human lung carcinoma cell line A549 was obtained from the American Type Culture Collection (ATCC) (Manassas, Va.). A549 cells were routinely cultured in DMEM basal media supplemented with 10% fetal bovine serum, 100 units per mL penicillin, and 100 micrograms per mL streptomycin (media and supplements from Invitrogen Life Technologies, Carlsbad, Calif.). Cells were routinely passaged by trypsinization and dilution when they reached approximately 90% confluence.

For Northern blotting or other analysis, cells may be seeded onto 100 mm or other standard tissue culture plates and treated similarly, using appropriate volumes of medium and oligonucleotide.

Treatment with Antisense Compounds:

When cells reached 65-75% confluency, they were treated with oligonucleotide. Oligonucleotide was mixed with LIPOFECTIN® Invitrogen Life Technologies, Carlsbad, Calif.) in OPTI-MEM® 1 reduced serum medium (Invitrogen Life Technologies, Carlsbad, Calif.) to achieve the desired concentration of oligonucleotide and a LIPOFECTIN® concentration of 2.5 or 3 μg/mL per 100 nM oligonucleotide. This transfection mixture was incubated at room temperature for approximately 0.5 hours. For cells grown in 96-well plates, wells were washed once with 100 μL OPTI-MEM® 1 and then treated with 130 μL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh culture medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Aurora B Expression

Antisense modulation of Aurora B expression can be assayed in a variety of ways known in the art. For example, Aurora B mRNA levels can be quantitated by, e.g., Northern blot analysis, competitive polymerase chain reaction (PCR), or quantitative real-time PCR. Quantitative real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM® 7600, 7700, or 7900 Sequence Detection System, available from PE-Applied Biosystems, Foster City, Calif. and used according to manufacturer's instructions.

Protein levels of Aurora B can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to Aurora B can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays for the Use of Aurora B Inhibitors

Once Aurora B inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of Aurora B in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with Aurora B inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the Aurora B inhibitors. Hallmark genes, or those genes suspected to be associated with a specific disease state, condition, or phenotype, are measured in both treated and untreated cells.

Example 12

RNA Isolation

Poly(A)+ mRNA Isolation

Poly(A)+mRNA was isolated according to Miura et al., (*Clin. Chem.*, 1996, 42, 1758-1764). Other methods for poly(A)+mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY® 96 kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY® 96 well plate attached to a QIAvac manifold fitted with a waste collection tray and attached to a vacuum source. Vacuum was applied for 1 minute. 500 µL of Buffer RW1 was added to each well of the RNEASY® 96 plate and incubated for 15 minutes and the vacuum was again applied for 1 minute. An additional 500 µL of Buffer RW1 was added to each well of the RNEASY® 96 plate and the vacuum was applied for 2 minutes. 1 mL of Buffer RPE was then added to each well of the RNEASY® 96 plate and the vacuum applied for a period of 90 seconds. The Buffer RPE wash was then repeated and the vacuum was applied for an additional 3 minutes. The plate was then removed from the QIAvac manifold and blotted dry on paper towels. The plate was then re-attached to the QIAvac manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN® Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Aurora B mRNA Levels

Quantitation of Aurora B mRNA levels was accomplished by real-time quantitative PCR using the ABI PRISM® 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM™ or JOE™ or VIC™ obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA™, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM® Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 µL PCR cocktail (2.5×PCR buffer minus $MgCl_2$, 6.6 mM $MgCl_2$, 375 µM each of DATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time PCR are normalized using either the expression level of GAPDH, a gene whose expression is constant, or by quantifying total RNA using RIBOGREEN® (Molecular Probes, Inc. Eugene, Oreg.). GAPDH expression is quantified by real time PCR, by being run simultaneously with the target, multiplexing, or separately. Total RNA is quantified using RIBOGREEN® RNA quantification reagent from Molecular Probes. Methods of RNA quantification by RIBOGREEN® are taught in Jones, L. J., et al, *Analytical Biochemistry*, 1998, 265, 368-374.

In this assay, 175 µL of RIBOGREEN® working reagent (RIBOGREEN® reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human Aurora B were designed to hybridize to a human Aurora B sequence, using published sequence information (GENBANK® accession number NM_004217.1, incorporated herein as SEQ ID NO: 4). For human Aurora B the PCR primers were:

forward primer: CAGCGAGTCCTCCGGAAA (SEQ ID NO: 5)
reverse primer: ACATTGGAGCGGCTCATGA (SEQ ID NO: 6) and the PCR probe was: FAM-AGCCTGTCAC-CCCATCTGCACTTGTC-TAMRA (SEQ ID NO: 7) where FAM™ is the fluorescent dye and TAMRA™ is the quencher dye. For human GAPDH the PCR primers were:
forward primer: GAAGGTGAAGGTCGGAGTC(SEQ ID NO: 8)
reverse primer: GAAGATGGTGATGGGATTTC (SEQ ID NO: 9) and the PCR probe was: 5' JOE-CAAGCTTC-CGTTCTCAGCC-TAMRA 3' (SEQ ID NO: 10) where JOE™ is the fluorescent reporter dye and TAMRATMis the quencher dye.

Example 14

Northern Blot Analysis of Aurora B mRNA Levels

Eighteen hours after antisense treatment, cell monolayers were washed twice with cold PBS and lysed in 1 mL RNAZOL® (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND®-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER® UV Crosslinker 2400 (Stratagene, Inc, La Jolla, Calif.) and then probed using QUICKHYB® hybridization solution (Stratagene, La Jolla, Calif.) using manufacturer's recommendations for stringent conditions.

To detect human Aurora B, a human Aurora B specific probe was prepared by PCR using the forward primer CAGCGAGTCCTCCGGAAA (SEQ ID NO: 5) and the reverse primer ACATTGGAGCGGCTCATGA (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER® and IMAGEQUANT® Software V3.3 (Molecular Dynamics, Sunnyvale, Calif.). Data was normalized to GAPDH levels in untreated controls.

Example 15

Antisense Inhibition of Human Aurora B Expression by Chimeric Phosphorothioate Oligonucleotides Having 2'-MOE Wings and a Deoxy Gap In accordance with the present invention, a series of antisense compounds was designed to target different regions of the human Aurora B RNA, using published sequences (GENBANK® accession number NM_004217.1, incorporated herein as SEQ ID NO: 4). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl nucleotides, also known as 2'-MOE nucleotides. The internucleoside (backbone) linkages are phosphorothioate (P=S) throughout the oligonucleotide. All cytidine residues are 5-methylcytidines. The compounds were analyzed for their effect on human Aurora B mRNA levels by quantitative real-time PCR as described in other examples herein. Data are averages from two experiments in which T-24 cells were treated with the 100 nM of the antisense oligonucleotides of the present invention. The control oligonucleotide used in this assay was SEQ ID NO: 2. If present, "N.D." indicates "no data".

TABLE 1

Inhibition of human Aurora B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 173812 | Coding | 4 | 239 | GATGTCGGGTGTCCCACTGC | 33 | 11 |
| 173813 | Coding | 4 | 413 | CTCTCTGCGCAGCTGATGCT | 62 | 12 |
| 173814 | Coding | 4 | 739 | CACATTGTCTTCCTCCTCAG | 30 | 13 |
| 173815 | 3'UTR | 4 | 1196 | TTCAGCCTTTATTAAACAAA | 57 | 14 |
| 173816 | Coding | 4 | 554 | AAATGTGCAGCTCTTCTGCA | 41 | 15 |
| 173817 | Coding | 4 | 343 | ATGAAATGGCTTTTCTTCTC | 17 | 16 |
| 173818 | Coding | 4 | 268 | AAGTCATCAATTGTGAAGTG | 38 | 17 |
| 173819 | Coding | 4 | 677 | CTCTCCCTTGAGCCCTAAGA | 26 | 18 |
| 173820 | Coding | 4 | 714 | GCGCATGCACAGACCAGCCG | 58 | 19 |
| 173821 | Coding | 4 | 276 | CAATCTCAAAGTCATCAATT | 0 | 20 |
| 173822 | Coding | 4 | 464 | GTTGTAGAGACGCAGGATGT | 61 | 21 |
| 173823 | Coding | 4 | 484 | CTCCTCCGGTCATAAAAATA | 26 | 22 |
| 173824 | Stop Codon | 4 | 1080 | GGGACCATCAGGCGACAGAT | 53 | 23 |
| 173825 | Coding | 4 | 569 | TGTTCGCTGCTCGTCAAATG | 27 | 24 |
| 173826 | Coding | 4 | 681 | TCAGCTCTCCCTTGAGCCCT | 24 | 25 |
| 173827 | Coding | 4 | 318 | CCAAGTACACGTTTCCAAAC | 36 | 26 |
| 173828 | Coding | 4 | 963 | TGAGCAGTTTGGAGATGAGG | 38 | 27 |
| 173829 | Stop Codon | 4 | 1083 | ACAGGGACCATCAGGCGACA | 51 | 28 |
| 173830 | Start Codon | 4 | 52 | TCCTTCTGGGCCATCCTTAG | 51 | 29 |
| 173831 | Coding | 4 | 719 | GGAGGGCGCATGCACAGACC | 63 | 30 |
| 173832 | Coding | 4 | 259 | ATTGTGAAGTGCCGCGTTAA | 52 | 31 |
| 173833 | Start Codon | 4 | 60 | AGGAGTTCTCCTTCTGGGCC | 37 | 32 |
| 173834 | Coding | 4 | 887 | GCGATAGGTCTCGTTGTGTG | 43 | 33 |
| 173835 | Coding | 4 | 622 | TTCTTCCCATGGCAGTACAT | 56 | 34 |

TABLE 1-continued

Inhibition of human Aurora B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 173836 | Start Codon | 4 | 42 | CCATCCTTAGAGAGAAAGGG | 40 | 35 |
| 173837 | Coding | 4 | 173 | GGAGCGGCTCATGAGGACAA | 92 | 36 |
| 173838 | 3'UTR | 4 | 1105 | AACACACGCACCCGAGTGAA | 59 | 37 |
| 173839 | Coding | 4 | 141 | TGACAGGCTCTTTCCGGAGG | 81 | 38 |
| 173840 | 5'UTR | 4 | 2 | GGCACTGCTACTCTCCCGGC | 75 | 39 |
| 173841 | Start Codon | 4 | 56 | GTTCTCCTTCTGGGCCATCC | 52 | 40 |
| 173842 | 3'UTR | 4 | 1129 | CCCCTATACATACACAGACA | 60 | 41 |
| 173843 | Coding | 4 | 678 | GCTCTCCCTTGAGCCCTAAG | 46 | 42 |
| 173844 | Coding | 4 | 936 | CTCCCGTGGGCACAGAAGCG | 40 | 43 |
| 173845 | Coding | 4 | 785 | CATGCGCCCCTCAATCATCT | 44 | 44 |
| 173846 | Coding | 4 | 314 | GTACACGTTTCCAAACTTGC | 63 | 45 |
| 173847 | Coding | 4 | 734 | TGTCTTCCTCCTCAGGGAGG | 25 | 46 |
| 173848 | Coding | 4 | 427 | GCCTGGATTTCGATCTCTCT | 73 | 47 |

As shown in Table 1, SEQ ID NOs 11, 12, 13, 14, 15, 17, 18, 19, 21, 22, 23, 24, 26, 27, 28, 29, 30, 31, 32, 33, 34, 35, 36, 37, 38, 39, 40, 41, 42, 43, 44, 45, 46 and 47 demonstrated at least 25% inhibition of human Aurora B expression in this assay and are therefore preferred. More preferred are SEQ ID NOs 39 and 47. The target regions to which these preferred sequences are complementary are herein referred to as "preferred target segments" and are therefore preferred for targeting by compounds of the present invention. These preferred target segments are shown in Table 2. These sequences are shown to contain thymine (T) but one of skill in the art will appreciate that thymine (T) is generally replaced by uracil (U) in RNA sequences. The sequences represent the reverse complement of the preferred antisense compounds shown in Table 1. "Target site" indicates the first (5'-most) nucleotide number on the particular target nucleic acid to which the oligonucleotide binds. Also shown in Table 2 is the species in which each of the preferred target segments was found.

TABLE 2

Sequence and position of preferred target segments identified in Aurora B.

| SITE ID | TARGET SEQ ID NO | TARGET SITE | SEQUENCE | REV COMP OF SEQ ID | ACTIVE IN | SEQ ID NO |
|---|---|---|---|---|---|---|
| 88962 | 4 | 239 | gcagtgggacacccgacatc | 11 | H. sapiens | 48 |
| 88963 | 4 | 413 | agcatcagctgcgcagagag | 12 | H. sapiens | 49 |
| 88964 | 4 | 739 | ctgaggaggaagacaatgtg | 13 | H. sapiens | 50 |
| 88965 | 4 | 1196 | tttgtttaataaaggctgaa | 14 | H. sapiens | 51 |
| 88966 | 4 | 554 | tgcagaagagctgcacattt | 15 | H. sapiens | 52 |
| 88968 | 4 | 268 | cacttcacaattgatgactt | 17 | H. sapiens | 53 |
| 88969 | 4 | 677 | tcttagggctcaagggagag | 18 | H. sapiens | 54 |
| 88970 | 4 | 714 | cggctggtctgtgcatgcgc | 19 | H. sapiens | 55 |
| 88972 | 4 | 464 | acatcctgcgtctctacaac | 21 | H. sapiens | 56 |

TABLE 2-continued

Sequence and position of preferred target segments identified in Aurora B.

| SITE ID | TARGET SEQ ID NO | TARGET SITE | SEQUENCE | REV COMP OF SEQ ID | ACTIVE IN | SEQ ID NO |
|---|---|---|---|---|---|---|
| 88973 | 4 | 484 | tatttttatgaccggaggag | 22 | H. sapiens | 57 |
| 88974 | 4 | 1080 | atctgtcgcctgatggtccc | 23 | H. sapiens | 58 |
| 88975 | 4 | 569 | catttgacgagcagcgaaca | 24 | H. sapiens | 59 |
| 88977 | 4 | 318 | gtttggaaacgtgtacttgg | 26 | H. sapiens | 60 |
| 88978 | 4 | 963 | cctcatctccaaactgctca | 27 | H. sapiens | 61 |
| 88979 | 4 | 1083 | tgtcgcctgatggtccctgt | 28 | H. sapiens | 62 |
| 88980 | 4 | 52 | ctaaggatgcccagaagga | 29 | H. sapiens | 63 |
| 88981 | 4 | 719 | ggtctgtgcatgcgcctcc | 30 | H. sapiens | 64 |
| 88982 | 4 | 259 | ttaacgcggcacttcacaat | 31 | H. sapiens | 65 |
| 88983 | 4 | 60 | ggcccagaaggagaactcct | 32 | H. sapiens | 66 |
| 88984 | 4 | 887 | cacacaacgagacctatcgc | 33 | H. sapiens | 67 |
| 88985 | 4 | 622 | atgtactgccatgggaagaa | 34 | H. sapiens | 68 |
| 88986 | 4 | 42 | ccctttctctctaaggatgg | 35 | H. sapiens | 69 |
| 88987 | 4 | 173 | ttgtcctcatgagccgctcc | 36 | H. sapiens | 70 |
| 88988 | 4 | 1105 | ttcactcgggtgcgtgtgtt | 37 | H. sapiens | 71 |
| 88989 | 4 | 141 | cctccggaaagagcctgtca | 38 | H. sapiens | 72 |
| 88990 | 4 | 2 | gccgggagagtagcagtgcc | 39 | H. sapiens | 73 |
| 88991 | 4 | 56 | ggatgcccagaaggagaac | 40 | H. sapiens | 74 |
| 88992 | 4 | 1129 | tgtctgtgtatgtatagggg | 41 | H. sapiens | 75 |
| 88993 | 4 | 678 | cttagggctcaagggagagc | 42 | H. sapiens | 76 |
| 88994 | 4 | 936 | cgcttctgtgcccacgggag | 43 | H. sapiens | 77 |
| 88995 | 4 | 785 | agatgattgaggggcgcatg | 44 | H. sapiens | 78 |
| 88996 | 4 | 314 | gcaagtttggaaacgtgtac | 45 | H. sapiens | 79 |
| 88997 | 4 | 734 | cctccctgaggaggaagaca | 46 | H. sapiens | 80 |
| 88998 | 4 | 427 | agagagatcgaaatccaggc | 47 | H. sapiens | 81 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically According to the present invention, antisense compounds include antisense oligomeric compounds, antisense oligonucleotides, siRNAs, external guide sequence (EGS) oligonucleotides, alternate splicers, and other short oligomeric compounds which hybridize to at least a portion of the target nucleic acid.

Example 16

Western Blot Analysis of Aurora B Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to Aurora B is used, with a radiolabeled or fluorescently labeled secondary antibody directed against the primary antibody species. Bands are visualized using a PHOSPHORIMAGER™ (Molecular Dynamics, Sunnyvale Calif.).

Example 17

Antisense Inhibition of Aurora B in Functional Assays

Functional assays are used to evaluate how gene expression affects cellular pathways and metabolic processes. In a further embodiment, a variety of functional assays were performed to investigate how Aurora B participates in cell proliferation and survival, adipocytes differentiation and the inflammatory response. Such assays can be used, by way of example, to determine the function of Aurora B in different cellular pathways and metabolic processes and to identify new therapeutic areas where inhibition of Aurora B can be beneficial.

Cell Proliferation

Cell cycle regulation is the basis for various cancer therapeutics. Unregulated cell proliferation is a characteristic of cancer cells, thus most current chemotherapy agents target dividing cells, for example, by blocking the synthesis of new DNA required for cell division. However, cells in healthy tissues are also affected by agents that modulate cell proliferation.

In some cases, a cell cycle inhibitor will cause apoptosis in cancer cells, but allow normal cells to undergo growth arrest and therefore remain unaffected (Blagosklonny, *Bioessays*, 1999, 21, 704-709; Chen et al., *Cancer Res.*, 1997, 57, 2013-2019; Evan and Littlewood, *Science*, 1998, 281, 1317-1322; Lees and Weinberg, *Proc. Natl. Acad. Sci. USA*, 1999, 96, 4221-4223). An 281, 1317-1322; Lees and Weinberg, *Proc. Natl. Acad. Sci. USA*, 1999, 96, 4221-4223). An example of sensitization to anti-cancer agents is observed in cells that have reduced or absent expression of the tumor suppressor genes p53 (Bunz et al., *Science*, 1998, 282, 1497-1501; Bunz et al., *J. Clin. Invest.*, 1999, 104, 263-269; Stewart et al., *Cancer Res.*, 1999, 59, 3831-3837; Wahl et al., *Nat. Med.*, 1996, 2, 72-79). However, cancer cells often escape apoptosis (Lowe and Lin, *Carcinogenesis*, 2000, 21, 485-495; Reed, *Cancer J. Sci. Am.*, 1998, 4 Suppl 1, S8-14). Further disruption of cell cycle checkpoints in cancer cells can increase sensitivity to chemotherapy while allowing normal cells to take refuge in G1 and remain unaffected. Cell cycle assays are employed to identify genes, such as p53, whose inhibition will sensitize cells to anti-cancer agents.

In a further embodiment of the invention, a cell cycle assay was conducted to investigate the effects of antisense inhibition of Aurora B on cell cycle progression in normal human mammary epithelial cells (HMECs) as well as two breast carcinoma cell lines, MCF7 and T47D. All of the cell lines are obtained from the American Type Culture Collection (Manassas, Va.). The latter two cell lines express similar genes but MCF7 cells express the tumor suppressor p53, while T47D cells are deficient in p53. Also used in this assay were T47Dp53 cells, which are T47D cells that have been transfected with and selected for maintenance of a plasmid that expresses a wildtype copy of the p53 gene (for example, pCMV-p53; Clontech, Palo Alto, Calif.), using standard laboratory procedures.

MCF-7 and HMECs cells are routinely cultured in DMEM low glucose (Invitrogen Life Technologies, Carlsbad, Calif.) supplemented with 10% fetal bovine serum (Invitrogen Life Technologies, Carlsbad, Calif.). T47D and T47Dp53 cells were cultured in DMEM High glucose media (Invitrogen Life Technologies, Carlsbad, Calif.) supplemented with 10% fetal bovine serum. Cells were routinely passaged by trypsinization and dilution when they reached approximately 90% confluence. Cells were plated in 24-well plates at approximately 50,000-60,000 cells per well for HMEC cells, approximately 140,000 cells per well for MCF-7 and approximately 170,000 cells per well for T47D and T47Dp53 cells, and allowed to attach to wells overnight prior to treatment with oligomeric compounds.

ISIS 173840 (SEQ ID NO: 39) was used to inhibit Aurora B mRNA expression. An oligonucleotide with a randomized sequence, ISIS 29848 (NNNNNNNNNNNNNNNNNNNN; where N is A,T,C or G; herein incorporated as SEQ ID NO: 82) was used a negative control, a compound that does not modulate cell cycle progression. In addition, a positive control for the inhibition of cell proliferation was assayed. The positive control was ISIS 183881 (ATCCAAGTGC-TACTGTAGTA; herein incorporated as SEQ ID NO: 83) targets kinesin-like 1, a gene whose inhibition is known to cause cell cycle arrest. ISIS 29248 and ISIS 183881 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Oligonucleotide was mixed with LIPOFECTIN® (Invitrogen Life Technologies, Carlsbad, Calif.) in OPTI-MEM® 1 (Invitrogen Life Technologies, Carlsbad, Calif.) to acheive a final concentration of 200 nM of oligonucleotide and 6 μg/mL LIPOFECTIN®. Before adding to cells, the oligonucleotide, LIPOFECTIN® and OPTI-MEM® 1 were mixed thoroughly and incubated for 0.5 hrs. The medium was removed from the plates and the plates were tapped on sterile gauze. Each well containing T47D or MCF7 cells was washed with 150 μl of phosphate-buffered saline. Each well containing HMECs was washed with 150 μL of Hank's balanced salt solution. The wash buffer in each well was replaced with 100 μL of the oligonucleotide/OPTI-MEM® 1/LIPOFECTIN® cocktail. Control cells received LIPO-FECTIN® only. The plates were incubated for approximately 4 hours at 37° C., after which the medium was removed and the plate was tapped on sterile gauze. 100 μl of full growth medium was added to each well. After approximately 72 hours, routine procedures were used to prepare cells for flow cytometry analysis and cells were stained with propidium iodide to generate a cell cycle profile using a flow cytometer. The cell cycle profile was analyzed with the MODFIT™ program (Verity Software House, Inc., Topsham Me.).

Fragmentation of nuclear DNA is a hallmark of apoptosis and produces an increase in cells with a hypodiploid DNA content, which are categorized as "subG1". An increase in cells in G1 phase is indicative of a cell cycle arrest prior to entry into S phase; an increase in cells in S phase is indicative of cell cycle arrest during DNA synthesis; and an increase in cells in the G2/M phase is indicative of cell cycle arrest just prior to or during mitosis.

Presented in Table 3 are the results of the cell cycle assay performed as described in MCF7, T47D and HMEC cells. Data are expressed as percentage of cells in each phase relative to the cell cycle profile of untreated control cells. A value above or below 100% indicates an increase or decrease, respectively, in the percentage of cells in the indicated cell cycle phase, relative to untreated control samples.

TABLE 3

Cell cycle profile of cells treated with oligomeric compounds targeted to Aurora B

| Cell Type | Treatment | Target | Sub G1 | G1 Phase | S Phase | G2/M Phase |
|---|---|---|---|---|---|---|
| MCF7 | ISIS 173840 | Aurora B | 91 | 108 | 84 | 109 |
|  | ISIS 29848 | negative control | 75 | 103 | 93 | 103 |
|  | ISIS 183881 | positive control | 143 | 91 | 86 | 155 |
| T47D | ISIS 173840 | Aurora B | 140 | 82 | 77 | 161 |
|  | ISIS 29848 | negative control | 103 | 92 | 86 | 130 |
|  | ISIS 183881 | positive control | 206 | 68 | 70 | 201 |
| HMEC | ISIS 173840 | Aurora B | 237 | 91 | 91 | 150 |
|  | ISIS 29848 | negative control | 140 | 100 | 82 | 120 |
|  | ISIS 183881 | positive control | 300 | 82 | 94 | 189 |

These data demonstrate that antisense inhibition of Aurora B in MCF7 cells results in no significant change in cell cycle profile. In T47D cells, antisense inhibition of Aurora B causes increases in the SubG1 and G2/M populations, and decreases in the G1 and S phases. Similarly, HMEC cells exhibit increases in the SubG1 and G2/M phases, and decreases in the G1 and S phases, following antisense inhibition of Aurora B. The difference between the effects on MCF7 and T47D cells is particularly interesting since T47D cells have a mutant p53 gene. This observation suggests that inhibition of Aurora B with ISIS 173840 preferentially inhibits the growth of cancer cells that have a mutation in p53.

The cell cycle assay was also performed in T47Dp53 cells, which have a wild-type p53 gene, to test whether the reintroduction of p53 affects the sensitivity of the cells to antisense inhibition of Aurora B. The data from this study are shown in Table 4. The assay was repeated in the T47D cells for comparison, and these data are also shown in Table 4.

TABLE 4

Effects of a functional p53 gene on cell cycle profiles following antisense inhibition of Aurora B

| Cell Type | Treatment | Target | Sub G1 | G1 Phase | S Phase | G2/M Phase |
|---|---|---|---|---|---|---|
| T47D | ISIS 173840 | Aurora B | 203 | 92 | 68 | 191 |
|  | ISIS 29848 | negative control | 197 | 94 | 94 | 130 |
|  | ISIS 183881 | positive control | 321 | 88 | 71 | 197 |
| T47Dp53 | ISIS 173840 | Aurora B | 235 | 90 | 99 | 137 |
|  | ISIS 29848 | negative control | 123 | 99 | 101 | 99 |
|  | ISIS 183881 | positive control | 302 | 73 | 89 | 225 |

These data demonstrate that, in the absence of a wild-type p53 gene, antisense inhibition of Aurora B in T47D cells leads to a greater G2/M phase arrest than in the presence of functional p53. Thus, the reintroduction of p53 into T47D cells resulted in decreased sensitivity of the cells to antisense inhibition of Aurora B, further demonstrating that modulation of Aurora B expression is in part dependent on p53. Therefore, the inhibition of Aurora B expression can be used to selectively modulate the growth of p53-deficient cells, such as cancer cells.

As antisense inhibition of Aurora B leads to a cell cycle arrest, oligomeric compounds targeting Aurora B are useful for the treatment of hyperproliferative disorders, including, but not limited to, breast cancer, pancreatic cancer, colon cancer, ovarian cancer, thyroid cancer, cervical cancer, prostate cancer, head and neck cancer, lung cancer, myelomas, hepatocellular carcinoma, lymphomas and leukemias.

Cell Survival

Programmed cell death, or apoptosis, is an important aspect of various biological processes, including normal cell turnover, as well as immune system and embryonic development. Apoptosis involves the activation of caspases, a family of intracellular proteases through which a cascade of events leads to the cleavage of a select set of proteins. The caspase family can be divided into two groups: the initiator caspases, such as caspase-8 and -9, and the executioner caspases, such as caspase-3, -6 and -7, which are activated by the initiator caspases. The caspase family contains at least 14 members, with differing substrate preferences (Thornberry and Lazebnik, *Science*, 1998, 281, 1312-1316). A caspase assay is utilized to identify genes whose inhibition selectively causes apoptosis in breast carcinoma cell lines, without affecting normal cells, and to identify genes whose inhibition results in cell death in the p53-deficient T47D cells, and not in the MCF7 cells which express p53 (Ross et al., *Nat. Genet.*, 2000, 24, 227-235; Scherf et al., *Nat. Genet.*, 2000, 24, 236-244). The chemotherapeutic drugs taxol, cisplatin, etoposide, gemcitabine, camptothecin, aphidicolin and 5-fluorouracil all have been shown to induce apoptosis in a caspase-dependent manner.

In a further embodiment, a caspase activity assay was performed to test the effects of antisense inhibition of Aurora B on apoptosis in normal human mammary epithelial cells (HMECs) as well as two breast carcinoma cell lines, MCF7 and T47D. All cells were cultured as described for the cell cycle assay in 96-well plates with black sides and flat, transparent bottoms (Corning Incorporated, Corning, N.Y.). DMEM media, with and without phenol red, were obtained from Invitrogen Life Technologies (Carlsbad, Calif.). MEGM media, with and without phenol red, were obtained from Cambrex Bioscience (Walkersville, Md.).

ISIS 173840 (SEQ ID NO: 39) was used to inhibit Aurora B mRNA expression. An oligonucleotide with a randomized sequence, ISIS 29848 (SEQ ID NO: 82) was used as a negative control, a compound that does not affect caspase activity. As a positive control for caspase activation, an oligonucleotide targeted to human Jagged2 ISIS 148715 (TTGTCCCAGTCCCAGGCCTC; herein incorporated as SEQ ID NO: 84) or human notch1 ISIS 226844 (GCCCTC-CATGCTGGCACAGG; herein incorporated as SEQ ID NO: 85) was also assayed. Inhibition of either of these genes is known to induce caspase activity, and subsequently, apoptosis. ISIS 148715 and ISIS 226844 are both chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Cells were treated as described for the cell cycle assay with 200 nM oligonucleotide in 6 μg/mL LIPOFECTIN®. Caspase-3 activity was evaluated with a fluorometric HTS Caspase-3 assay (Catalog # HTS02; EMD Biosciences, San Diego, Calif.) that detects cleavage after aspartate residues in the peptide sequence (DEVD). The DEVD substrate is labeled with a fluorescent molecule, which exhibits a blue to green shift in fluorescence upon cleavage by caspase-3. Active caspase-3 in the oligonucleotide treated cells is measured by this assay according to the manufacturer's instructions. Approximately 48 hours following oligonucleotide treatment, 50 uL of assay buffer containing 10 µM dithiothreitol was added to each well, followed by addition 20 uL of the caspase-3 fluorescent substrate conjugate. Fluorescence in wells was immediately detected (excitation/emission 400/505 nm) using a fluorescent plate reader (SPECTRAMAX® GEMINI XS, Molecular Devices, Sunnyvale, Calif.). The plate was covered and incubated at 37° C. for and additional three hours, after which the fluorescence was again measured (excitation/emission 400/505 nm). The value at time zero was subtracted from the measurement obtained at 3 hours. The measurement obtained from the untreated control cells was designated as 100% activity.

The experiment was replicated in each of the 3 cell types, HMECs, T47D and MCF7 and the results are shown in Table 5. From these data, values for caspase activity above or below 100% are considered to indicate that the compound has the ability to stimulate or inhibit caspase activity, respectively. The data are shown as percent increase in fluorescence relative to untreated control values.

TABLE 5

Effects of antisense inhibition of Aurora B on apoptosis in the caspase assay

| Cell Type | Treatment | Target | % Caspase activity relative to untreated control |
|---|---|---|---|
| HMEC | ISIS 173840 | Aurora B | 194 |
| | ISIS 148715 | positive control | 1183 |
| | ISIS 29848 | negative control | 133 |
| MCF7 | ISIS 173840 | Aurora B | 136 |
| | ISIS 226820 | positive control | 326 |
| | ISIS 29848 | negative control | 110 |
| T47D | ISIS 173840 | Aurora B | 144 |
| | ISIS 148715 | positive control | 594 |
| | ISIS 29848 | negative control | 134 |

Treatment of HMEC, MCF7, and T47D cells with ISIS 173840 resulted in an increase in caspase activity, suggesting an increase in apoptosis relative to the untreated control.

Adipocyte Assay

Insulin is an essential signaling molecule throughout the body, but its major target organs are the liver, skeletal muscle and adipose tissue. Insulin is the primary modulator of glucose homeostasis and helps maintain a balance of peripheral glucose utilization and hepatic glucose production. The reduced ability of normal circulating concentrations of insulin to maintain glucose homeostasis manifests in insulin resistance which is often associated with diabetes, central obesity, hypertension, polycystic ovarian syndrom, dyslipidemia and atherosclerosis (Saltiel, Cell, 2001, 104, 517-529; Saltiel and Kahn, Nature, 2001, 414, 799-806).

Insulin promotes the differentiation of preadipocytes into adipocytes. The condition of obesity, which results in increases in fat cell number, occurs even in insulin-resistant states in which glucose transport is impaired due to the antilipolytic effect of insulin. Inhibition of triglyceride breakdown requires much lower insulin concentrations than stimulation of glucose transport, resulting in maintenance or expansion of adipose stores (Kitamura et al., Mol. Cell. Biol., 1999, 19, 6286-6296; Kitamura et al., Mol. Cell. Biol., 1998, 18, 3708-3717).

One of the hallmarks of cellular differentiation is the upregulation of gene expression. During adipocyte differentiation, the gene expression patterns in adipocytes change considerably. Some genes known to be upregulated during adipocyte differentiation include hormone-sensitive lipase (HSL), adipocyte lipid binding protein (aP2), glucose transporter 4 (Glut4), and peroxisome proliferator-activated receptor gamma (PPAR-γ). Insulin signaling is improved by compounds that bind and inactivate PPAR-γ, a key regulator of adipocyte differentiation (Olefsky, J. Clin. Invest., 2000, 106, 467-472). Insulin induces the translocation of GLUT4 to the adipocyte cell surface, where it transports glucose into the cell, an activity necessary for triglyceride synthesis. In all forms of obesity and diabetes, a major factor contributing to the impaired insulin-stimulated glucose transport in adipocytes is the downregulation of GLUT4. Insulin also induces hormone sensitive lipase (HSL), which is the predominant lipase in adipocytes that functions to promote fatty acid synthesis and lipogenesis (Fredrikson et al., J. Biol. Chem., 1981, 256, 6311-6320). Adipocyte fatty acid binding protein (aP2) belongs to a multi-gene family of fatty acid and retinoid transport proteins. aP2 is postulated to serve as a lipid shuttle, solubilizing hydrophobic fatty acids and delivering them to the appropriate metabolic system for utilization (Fu et al., J. Lipid Res., 2000, 41, 2017-2023; Pelton et al., Biochem. Biophys. Res. Commun., 1999, 261, 456-458). Together, these genes play important roles in the uptake of glucose and the metabolism and utilization of fats.

Leptin secretion and an increase in triglyceride content are also well-established markers of adipocyte differentiation. While it serves as a marker for differentiated adipocytes, leptin also regulates glucose homeostasis through mechanisms (autocrine, paracrine, endocrine and neural) independent of the adipocyte's role in energy storage and release. As adipocytes differentiate, insulin increases triglyceride accumulation by both promoting triglyceride synthesis and inhibiting triglyceride breakdown (Spiegelman and Flier, Cell, 2001, 104, 531-543). As triglyceride accumulation correlates tightly with cell size and cell number, it is an excellent indicator of differentiated adipocytes.

In a further embodiment, the effects of antisense inhibition of Aurora B on the expression of markers of cellular differentiation were examined in preadipocytes, using an insulin signaling assay. Human white preadipocytes (Zen-Bio Inc., Research Triangle Park, NC) were grown in preadipocyte media (ZenBio Inc., Research Triangle Park, NC). One day before transfection, 96-well plates were seeded with approximately 3000 cells/well.

Cells were treated with ISIS 173840 (SEQ ID NO: 39) to inhibit Aurora B expression. An oligonucleotide with a randomized sequence, ISIS 29848 (SEQ ID NO: 82) was used a negative control, a compound that does not modulate adipocyte differentiation. Tumor necrosis factor alpha (TNF-α), which inhibits adipocyte differentiation, was used as a positive control for the inhibition of adipocyte differentiation as evaluated by leptin secretion. For all other parameters measured, ISIS 105990 (AGCAAAAGATCAATCCGTTA, incorporated herein as SEQ ID NO: 86), an inhibitor of PPAR-γ, served as a positive control for the inhibition of adipocyte differentiation. ISIS 105990 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Oligonucleotide was mixed with LIPOFECTIN® (Invitrogen Life Technologies, Carlsbad, Calif.) in OPTI-MEM® 1 (Invitrogen Life Technologies, Carlsbad, Calif.) to acheive a final concentration of 250 nM of oligonucleotide and 6.5 µg/mL LIPOFECTIN®. Before adding to cells, the oligonucleotide, LIPOFECTIN® and OPTI-MEM® 1 were mixed thoroughly and incubated for 0.5 hrs. Untreated control cells received LIPOFECTIN® only. The medium was removed from the plates and the plates were tapped on sterile gauze. Each well was washed in 150 µl of phosphate-buffered saline. The wash buffer in each well was replaced with 100 µL of the oligonucleotide/OPTI-MEM® 1/LIPOFECTIN® cocktail. Compounds of the invention and ISIS 105990 were tested in triplicate, ISIS 29848 was tested in up to six replicate wells. The plates were incubated for approximately 4 hours at 37° C., after which the medium was removed and the plate was tapped on sterile gauze. 100 µl of full growth medium was added to each well. After the cells have reached confluence (approximately three days), they were exposed for three days to differentiation media (Zen-Bio, Inc.) containing a PPAR-γ agonist, IBMX, dexamethasone, and insulin. Cells were then fed adipocyte media (Zen-Bio, Inc.), which was replaced at 2 to 3 day intervals.

Leptin secretion into the media in which adipocytes are cultured was measured by protein ELISA. On day nine post-transfection, 96-well plates were coated with a monoclonal antibody to human leptin (R&D Systems, Minneapolis, Minn.) and left at 4° C. overnight. The plates were blocked with bovine serum albumin (BSA), and a dilution of the treated adipoctye media was incubated in the plate at room temperature for approximately 2 hours. After washing to remove unbound components, a second monoclonal antibody to human leptin (conjugated with biotin) was added. The plate was then incubated with strepavidin-conjugated horse radish peroxidase (HRP) and enzyme levels were determined by incubation with 3,3',5,5'-tetramethlybenzidine, which turns blue when cleaved by HRP. The $OD_{450}$ was read for each well, where the dye absorbance is proportional to the leptin concentration in the cell lysate. Results, shown in Table 6, are expressed as a percent control relative to untreated control samples. With respect to leptin secretion, values above or below 100% are considered to indicate that the compound has the ability to stimulate or inhibit leptin secretion, respectively.

The triglyceride accumulation assay measures the synthesis of triglyceride by adipocytes. Triglyceride accumulation is measured using the Infinity™ Triglyceride reagent kit (Sigma-Aldrich, St. Louis, Mo.). On day nine post-transfection, cells are washed and lysed at room temperature, and the triglyceride assay reagent is added. Triglyceride accumulation is measured based on the amount of glycerol liberated from triglycerides by the enzyme lipoprotein lipase. Liberated glycerol is phosphorylated by glycerol kinase, and hydrogen peroxide is generated during the oxidation of glycerol-1-phosphate to dihydroxyacetone phosphate by glycerol phosphate oxidase. Horseradish peroxidase (HRP) uses $H_2O_2$ to oxidize 4-aminoantipyrine and 3,5 dichloro-2-hydroxybenzene sulfonate to produce a red-colored dye. Dye absorbance, which is proportional to the concentration of glycerol, is measured at 515 nm using an UV spectrophotometer. Glycerol concentration is calculated from a standard curve for each assay, and data are normalized to total cellular protein as determined by a Bradford assay (Bio-Rad Laboratories, Hercules, Calif.). Results, shown in Table 6, are expressed as a percent control relative to untreated control samples. With respect to triglyceride accumulation, values above or below 100% are considered to indicate that the compound has the ability to stimulate or inhibit triglyceride accumulation, respectively.

Expression of the four hallmark genes, HSL, aP2, Glut4, and PPAR-γ, was also measured in adipocytes treated with oligomeric compounds. Cells were lysed on day nine post-transfection, in a guanadinium-containing buffer and total RNA was harvested. The amount of total RNA in each sample was determined using a Ribogreen Assay (Invitrogen Life Technologies, Carlsbad, Calif.). Real-time PCR was performed on the total RNA using primer/probe sets for the adipocyte differentiation hallmark genes Glut4, HSL, aP2, and PPAR-γ. mRNA levels, shown in Table 6, are expressed as percent control relative to the untreated control values. The data for these markers represents the average of 2 assays. With respect to the four adipocyte differentiation hallmark genes, values above or below 100% are considered to indicate that the compound has the ability to stimulate or inhibit adipocyte differentiation, respectively.

TABLE 6

Effects of antisense inhibition of Aurora B on adipocyte differentiation

| Treatment | Target | Triglyceride accumulation | Leptin secretion | aP2 | Glut4 | HSL | PPARγ |
|---|---|---|---|---|---|---|---|
| ISIS 173840 | Aurora B | 53 | 122 | 37 | 29 | 19 | 72 |
| ISIS 29848 | negative control | 74 | 103 | 77 | 74 | 77 | 86 |
| ISIS 105990 | positive control | 16 | N.D. | 36 | 29 | 35 | 43 |
| TNF-alpha | positive control | N.D. | 32 | N.D. | N.D. | N.D. | N.D. |

Treatment of adipocytes with ISIS 173840 markedly reduced triglyceride accumulation and inhibited the upregulation of all 4 hallmark genes tested, suggesting an inhibition of adipocyte differentiation. In particular, the expression of aP2, Glut4 and HSL were significantly lowered following antisense inhibition of Aurora B. Leptin secretion was increased following antisense inhibition of Aurora B.

Inflammation Assays

Inflammation assays are designed to identify genes that regulate the activation and effector phases of the adaptive immune response. During the activation phase, T lymphocytes (also known as T-cells) receiving signals from the appropriate antigens undergo clonal expansion, secrete cytokines, and upregulate their receptors for soluble growth factors, cytokines and co-stimulatory molecules (Cantrell, Annu. Rev. Immunol., 1996, 14, 259-274). These changes drive T-cell differentiation and effector function. In the effector phase, response to cytokines by non-immune effector cells controls the production of inflammatory mediators that can do extensive damage to host tissues. The cells of the adaptive immune systems, their products, as well as their interactions with various enzyme cascades involved in inflammation (e.g., the complement, clotting, fibrinolytic and kinin cascades) all represent potential points for intervention in inflammatory disease. The inflammation assay presented here measures hallmarks of the activation phase of the immune response.

Dendritic cells treated with antisense compounds are used to identify regulators of dendritic cell-mediated T-cell costimulation. The level of interleukin-2 (IL-2) production by T-cells, a critical consequence of T-cell activation (DeSilva et al., *J. Immunol.*, 1991, 147, 3261-3267; Salomon and Bluestone, *Annu. Rev. Immunol.*, 2001, 19, 225-252), is used as an endpoint for T-cell activation. T lymphocytes are important immunoregulatory cells that mediate pathological inflammatory responses. Optimal activation of T lymphocytes requires both primary antigen recognition events as well as secondary or costimulatory signals from antigen presenting cells (APC). Dendritic cells are the most efficient APCs known and are principally responsible for antigen presentation to T-cells, expression of high levels of costimulatory molecules during infection and disease, and the induction and maintenance of immunological memory (Banchereau and Steinman, *Nature*, 1998, 392, 245-252). While a number of costimulatory ligand-receptor pairs have been shown to influence T-cell activation, a principal signal is delivered by engagement of CD28 on T-cells by CD80 (B7-1) and CD86 (B7-2) on APCs (Boussiotis et al., *Curr. Opin. Immunol.*, 1994, 6, 797-807; Lenschow et al., *Annu. Rev. Immunol.*, 1996, 14, 233-258). Inhibition of T-cell co-stimulation by APCs holds promise for novel and more specific strategies of immune suppression. In addition, blocking costimulatory signals may lead to the development of long-term immunological anergy (unresponsiveness or tolerance) that would offer utility for promoting transplantation or dampening autoimmunity. T-cell anergy is the direct consequence of failure of T-cells to produce the growth factor IL-2 (DeSilva et al., *J. Immunol.*, 1991, 147, 3261-3267; Salomon and Bluestone, *Annu. Rev. Immunol.*, 2001, 19, 225-252).

In a further embodiment of the present invention, the effect of ISIS 173840 (SEQ ID NO: 39) was examined on the dendritic cell-mediated costimulation of T-cells. Dendritic cells (DCs, Clonetics Corp., San Diego, Calif.) were plated at approximately 6500 cells/well on anti-CD3 (UCHT1, Pharmingen-BD, San Diego, Calif.) coated 96-well plates in 500 U/mL granulocyte macrophase-colony stimulation factor (GM-CSF) and interleukin-4 (IL-4). DCs were treated with antisense compounds approximately 24 hours after plating.

Cells were treated with ISIS 173840 (SEQ ID NO: 39) to inhibit Aurora B expression. An oligonucleotide with a randomized sequence, ISIS 29848 (SEQ ID NO: 82) served as a negative control, a compound that does not affect dendritic cell-mediated T-cell costimulation. ISIS 113131 (CGTGTGTCTGTGCTAGTCCC, incorporated herein as SEQ ID NO: 87), an inhibitor of CD86, served as a positive control for the inhibition of dendritic cell-mediated T-cell costimulation ISIS 113131 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Oligonucleotide was mixed with LIPOFECTIN® (Invitrogen Life Technologies, Carlsbad, Calif.) in OPTI-MEM® 1 (Invitrogen Life Technologies, Carlsbad, Calif.) to acheive a final concentration of 200 nM of oligonucleotide and 6 μg/mL LIPOFECTIN®. Before adding to cells, the oligonucleotide, LIPOFECTIN® and OPTI-MEM® 1 were mixed thoroughly and incubated for 0.5 hrs. The medium was removed from the cells and the plates were tapped on sterile gauze. Each well was washed in 150 μl of phosphate-buffered saline. The wash buffer in each well was replaced with 100 μL of the oligonucleotide/OPTI-MEM® 1/LIPOFECTIN® cocktail. Untreated control cells received LIPOFECTIN® only. ISIS 173840 and ISIS 113131 were tested in triplicate, and the negative control oligonucleotide was tested in up to six replicates. The plates were incubated with oligonucleotide for approximately 4 hours at 37° C., after which the medium was removed and the plate was tapped on sterile gauze. Fresh growth media plus cytokines was added and DC culture was continued for an additional 48 hours. DCs are then co-cultured with Jurkat T-cells in RPMI medium (Invitrogen Life Technologies, Carlsbad, Calif.) supplemented with 10% heat-inactivated fetal bovine serum (Sigma Chemical Company, St. Louis, Mo.). Culture supernatants are collected approximately 24 hours later and assayed for IL-2 levels (IL-2 DuoSet, R&D Systems, Minneapolis, Minn.), which are expressed as a percent relative to untreated control samples. A value greater than 100% indicates an induction of the inflammatory response, whereas a value less than 100% demonstrates a reduction in the inflammatory response.

The culture supernatant of cells treated with ISIS 173840, ISIS 113131 and ISIS 29848 contained IL-2 at 85%, 56%, and 92% of the IL-2 concentration found in culture supernatant from untreated control cells, respectively, suggesting that ISIS 173840 inhibited T-cell co-stimulation. As such, antisense oligonucleotides targeting Aurora B are candidate therapeutic compounds with applications in the prevention, treatment or attenuation of conditions associated with hyperstimulation of the immune system, including rheumatoid arthritis, irritable bowel disease, athsma, lupus and multiple sclerosis.

What is claimed is:

1. A chemically modified antisense compound 13 to 40 nucleobases in length targeted to a nucleic acid molecule encoding Aurora B (SEQ ID NO:4), wherein said compound is specifically hybridizable with said nucleic acid molecule encoding Aurora B, and wherein said antisense compound comprises at least an 8 nucleobase portion of SEQ ID NO: 12.

2. The antisense compound of claim 1, wherein said antisense compound has a sequence consisting of SEQ ID NO 12.

3. The antisense compound of claim 2 which is single-stranded.

4. A chemically modified antisense compound 13 to 40 nucleobases in length targeted to a nucleic acid molecule encoding Aurora B (SEQ ID NO:4), wherein said compound is specifically hybridizable with said nucleic acid molecule encoding Aurora B, and wherein said antisense compound comprises at least an 8-nucleobase portion of SEQ ID NO: 47.

5. The antisense compound of claim 4, wherein said antisense compound has a sequence consisting of SEQ ID NO: 47.

6. The antisense compound of claim 5 which is single-stranded.

7. The modified antisense compound of claim 1, wherein the modified antisense compound comprises:
   a gap segment consisting of linked deoxynucleotides;
   a 5' wing segment consisting of linked nucleotides;
   a 3' wing segment consisting of linked nucleotides;
   wherein the gap segment is positioned between the 5' wing segment and the 3' wing segment and wherein each nucleotide of each wing segment comprises a modified sugar.

8. The modified antisense compound of claim 2, wherein the modified oligonucleotide comprises:
   a gap segement consisting often linked deoxynucleotides;
   a 5' wing segment consisting of five linked nucleotides;
   a 3' wing segment consisting of five linked nucleotides;
   wherein the gap segment is positioned between the 5' wing segment and the 3' wing segment, wherein each nucleotide of each wing segment comprises a 2'-O-methoxyethyl sugar; and wherein each internucleoside linkage is a phosphorothioate linkage.

9. The modified antisense compound of claim 4, wherein the modified antisense compound comprises:
  a gap segment consisting of linked deoxynucleotides;
  a 5' wing segment consisting of linked nucleotides;
  a 3' wing segment consisting of linked nucleotides;
  wherein the gap segment is positioned between the 5' wing segment and the 3' wing segment and wherein each nucleotide of each wing segment comprises a modified sugar.

10. The modified antisense compound of claim 5, wherein the modified oligonucleotide comprises:
  a gap segement consisting often linked deoxynucleotides;
  a 5' wing segment consisting of five linked nucleotides;
  a 3' wing segment consisting of five linked nucleotides;
  wherein the gap segment is positioned between the 5' wing segment and the 3' wing segment, wherein each nucleotide of each wing segment comprises a 2'-O-methoxyethyl sugar; and wherein each internucleoside linkage is a phosphorothioate linkage.

* * * * *